US009757266B2

(12) United States Patent
Hoffman et al.

(10) Patent No.: US 9,757,266 B2
(45) Date of Patent: Sep. 12, 2017

(54) ORTHOTIC DEVICE

(75) Inventors: Henry B. Hoffman, Charlotte, NC (US); G. Peter Macon, Davidson, NC (US); David Kirkland, Campbell, CA (US); Matthew Spencer, New York, NY (US); Linda Koh, Glenview, IL (US); Douglas Poe, Mahomet, IL (US)

(73) Assignee: Saebo, Inc., Charlotte, NC (US)

( * ) Notice: Subject to any disclaimer, the term of this patent is extended or adjusted under 35 U.S.C. 154(b) by 905 days.

(21) Appl. No.: 13/149,307

(22) Filed: May 31, 2011

(65) Prior Publication Data

US 2012/0059298 A1 Mar. 8, 2012

Related U.S. Application Data

(60) Provisional application No. 61/350,358, filed on Jun. 1, 2010.

(51) Int. Cl.
*A61F 5/00* (2006.01)
*A61F 5/01* (2006.01)
(Continued)

(52) U.S. Cl.
CPC .......... *A61F 5/013* (2013.01); *A61B 5/04888* (2013.01); *A61N 1/36003* (2013.01); *A61N 1/36014* (2013.01)

(58) Field of Classification Search
CPC .... A61F 5/013; A61F 5/0118; A61F 5/05875; A61N 1/36003; A61N 1/36014
USPC ...... 602/5, 16, 20-23, 2, 27-29; 607/46, 48, 607/49, 50, 52, 62, 77-78, 115; 623/24, 623/25, 57, 58, 59, 60, 61, 63, 65, 66;
(Continued)

(56) References Cited

U.S. PATENT DOCUMENTS 867,981 A 10/1907 Krizek
2,863,449 A 12/1958 Spencer
(Continued)

FOREIGN PATENT DOCUMENTS

CN 101433491 A 5/2009
DE 8804564.1 U1 9/1988
(Continued)

OTHER PUBLICATIONS

Search Report from corresponding European Application No. 05853749.9, dated Nov. 25, 2009.
(Continued)

*Primary Examiner* — Kim M Lewis
(74) *Attorney, Agent, or Firm* — Nelson Mullins Riley & Scarborough, LLP

(57) ABSTRACT

An orthotic device including a forearm support section configured to be releasably attached to a user's arm, a hand support section configured to be releasably attached to the user's hand, and an adjustable joint coupled to the forearm support section and the hand support section. At least one electromyography sensor is coupled to the forearm support section and positioned to sense activity of muscles in the user's arm, at least one electrode is coupled to the forearm support section and configured to provide electrical stimulation to muscles in the user's arm, and a controller is operatively coupled to the at least one electrode, the controller being configured to deliver electrical stimulation to the at least one electrode.

21 Claims, 16 Drawing Sheets

(51) Int. Cl.
*A61N 1/36* (2006.01)
*A61B 5/0488* (2006.01)

(58) Field of Classification Search
USPC .............. 600/595; 73/865.4, 379.01–379.09; 128/877–879; 482/8, 45–47, 27, 91, 114, 482/131
See application file for complete search history.

(56) References Cited

U.S. PATENT DOCUMENTS

| | | | |
|---|---|---|---|
| 3,631,542 A | 1/1972 | Potter | |
| 3,769,970 A | 11/1973 | Swanson | |
| 3,957,266 A | 5/1976 | Rice | |
| 4,173,021 A | 10/1979 | Zuchner et al. | |
| 4,602,620 A | 7/1986 | Marx | |
| 4,669,477 A | 6/1987 | Ober | |
| 4,765,320 A | 8/1988 | Lindemann et al. | |
| 4,772,012 A | 9/1988 | Chesher | |
| 4,781,178 A | 11/1988 | Gordon | |
| 4,790,301 A | 12/1988 | Silfverskiold | |
| 4,858,903 A | 8/1989 | Tari et al. | |
| 4,865,285 A | 9/1989 | Gaggianese | |
| 4,875,469 A | 10/1989 | Brook et al. | |
| 4,881,275 A | 11/1989 | Cazares et al. | |
| 4,945,902 A | 8/1990 | Dorer et al. | |
| 4,949,711 A | 8/1990 | Gyovai et al. | |
| 4,960,114 A | 10/1990 | Dale | |
| 4,977,890 A | 12/1990 | Mann | |
| 5,056,504 A | 10/1991 | Mann | |
| 5,156,168 A | 10/1992 | Canterna | |
| 5,162,030 A | 11/1992 | Tanski | |
| 5,205,812 A | 4/1993 | Wasserman | |
| 5,263,593 A | 11/1993 | Aida | |
| 5,295,948 A | 3/1994 | Gray | |
| 5,330,516 A | 7/1994 | Nathan | |
| 5,413,554 A | 5/1995 | Trueman | |
| 5,415,623 A | 5/1995 | Cherubini | |
| 5,415,624 A | 5/1995 | Williams | |
| 5,447,490 A | 9/1995 | Fula et al. | |
| 5,453,064 A | 9/1995 | Williams, Jr. | |
| 5,456,650 A | 10/1995 | Williams, Jr. et al. | |
| 5,505,553 A | 4/1996 | Saviano et al. | |
| 5,514,052 A | 5/1996 | Charles et al. | |
| 5,538,488 A | 7/1996 | Villepigue | |
| 5,542,667 A | 8/1996 | Lezdey et al. | |
| 5,560,375 A | 10/1996 | Kabanek | |
| 5,584,799 A | 12/1996 | Gray | |
| 5,599,123 A | 2/1997 | Still | |
| 5,637,078 A | 6/1997 | Varn | |
| 5,697,103 A | 12/1997 | Wiggins | |
| 5,807,293 A | 9/1998 | Wedge, Jr. | |
| 5,820,577 A | 10/1998 | Taylor | |
| 5,836,902 A | 11/1998 | Gray | |
| 5,876,363 A | 3/1999 | Marx | |
| 5,921,945 A | 7/1999 | Gary | |
| 6,016,103 A * | 1/2000 | Leavitt ........................ | 340/575 |
| 6,033,139 A | 3/2000 | Dutcher | |
| 6,379,393 B1 * | 4/2002 | Mavroidis et al. ............ | 623/25 |
| 6,456,885 B1 * | 9/2002 | Shiba et al. .................... | 607/48 |
| 6,561,995 B1 | 5/2003 | Thibodo, Jr. | |
| 6,575,926 B2 | 6/2003 | Bonutti | |
| 6,702,725 B2 | 3/2004 | Hoffman et al. | |
| 6,854,913 B2 | 2/2005 | Farrell et al. | |
| 7,001,352 B2 | 2/2006 | Farrell et al. | |
| 7,162,305 B2 * | 1/2007 | Tong et al. .................... | 607/48 |
| 2002/0077578 A1 | 6/2002 | Bonutti | |
| 2002/0198089 A1 | 12/2002 | Hoffman et al. | |
| 2003/0162634 A1 | 8/2003 | Farrell et al. | |
| 2003/0195093 A1 | 10/2003 | White | |
| 2003/0228185 A1 | 12/2003 | Farrell et al. | |
| 2004/0267331 A1 * | 12/2004 | Koeneman ............... | A61H 1/02 607/49 |
| 2006/0211964 A1 * | 9/2006 | Farrell et al. .................... | 602/5 |
| 2009/0149790 A1 | 6/2009 | Farrell et al. | |
| 2009/0326428 A1 | 12/2009 | Farrell et al. | |

FOREIGN PATENT DOCUMENTS

| | | |
|---|---|---|
| DE | 9204652.5 U1 | 7/1992 |
| KR | 20090088987 A | 8/2009 |
| WO | 9403238 A | 2/1994 |
| WO | 2006/022307 A1 | 3/2006 |
| WO | 2008036746 A2 | 3/2008 |

OTHER PUBLICATIONS

Office Action for European Application No. 05853749.9, dated Mar. 28, 2011.
International Search Report and Written Opinion for co-pending PCT Application No. PCT/US2011/038720, dated Sep. 21, 2011.
Supplemental European Search Report dated May 24, 2016 for EP Application No. 11790321.1.
European Search Report dated Dec. 22, 2015 for EP Application No. 11790321.1.

* cited by examiner

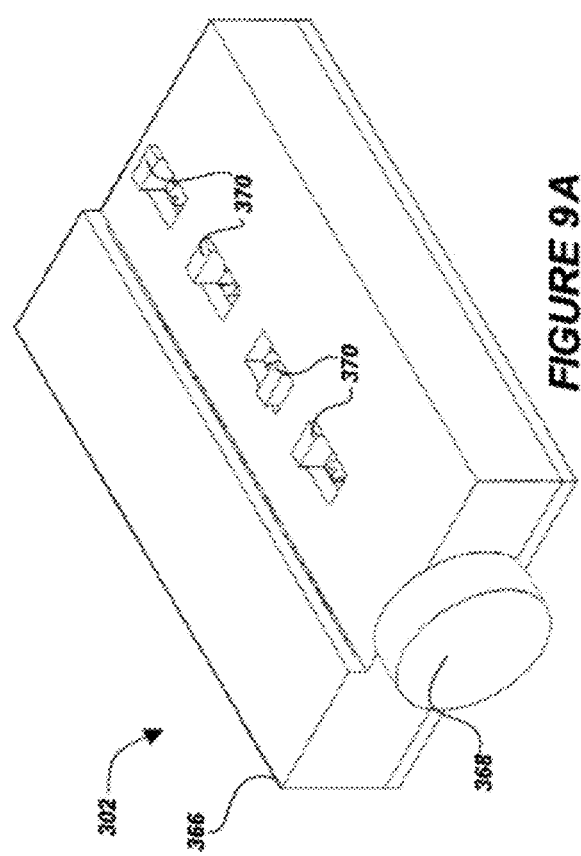
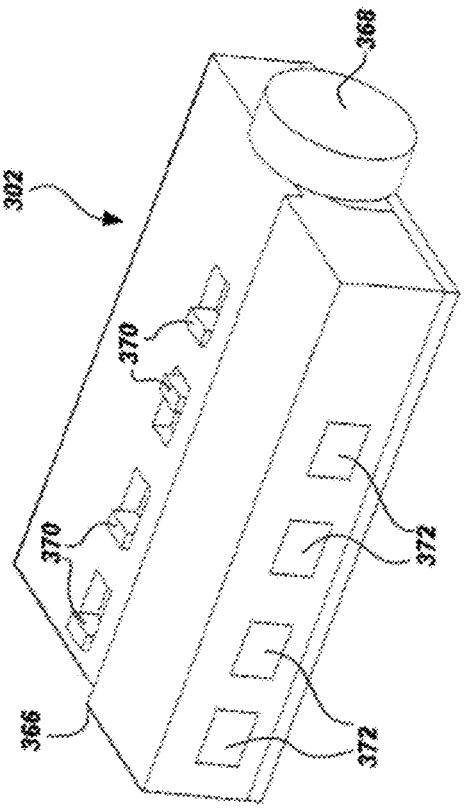
*FIGURE 9A*
*FIGURE 9B*

ORTHOTIC DEVICE

CLAIM OF PRIORITY

This application claims priority to U.S. Provisional Patent Application No. 61/350,358 filed Jun. 1, 2010, the entire disclosure of which is hereby incorporated by reference herein.

FIELD OF THE INVENTION

The present invention relates to the field of neurological rehabilitation device constructions in general, and more particularly to an electronic enabled neurological rehabilitation device.

BACKGROUND OF THE INVENTION

A dynamic wrist-hand-finger orthosis or splint is generally used for the positioning of an impaired, injured, or disabled wrist, hand, and fingers. Splints come in a variety of designs: static, static progressive, and dynamic that can be low profile or high profile. Most prior art splints are neurological in nature that either holds the hand in a static functional position, or uses a slight dynamic force to position the fingers.

Many people suffering a neurological injury from stroke, cerebral palsy, brain injury, etc., have upper extremity impairments. Many have some shoulder and elbow movements, but are unable to extend their wrist or fingers to grasp an object. This is usually due to hypertonicity, a condition where the flexor or extensor muscles in the upper extremities are spastic and resist positioning. Dynamic splints can be used to support or to hold joints in certain positions. An effective dynamic splint designed to be used for hypertonicity must offer enough force to balance the effects of the increased muscle tone. Also most current dynamic splints are used for orthopedic injuries and use a variety of finger cuffs to support the digits. These cuffs are not practical when working on a digit affected by hypertonicity, as they move proximal upon closing the fingers, and then have to be repositioned after opening the fingers manually.

Functional electrical stimulation ("FES") uses electrical currents to activate nerves innervating paretic muscles. The purpose of electrical stimulation is to decrease impairments and increase functional independence. Surface FES systems use controlled electrical currents through electrodes placed on the surface of the body, in order to trigger contraction from muscles underlying the electrode. FES may be used in prostheses for restoring active function to paralyzed or hypertonic body limbs. Unfortunately, with respect to the hand, patients that exhibit increased tone or hypertonicity are unable to effectively use electrical stimulation with or without current orthotics on the market. Neurological patients are unable to adequately extend their fingers, specifically at the PIP and DIP joints, when electrical stimulation is applied. One of the reasons for the lack of finger extension is due to wrist position. As the wrist moves from the flexion to extension, the fingers passively flex. This is phenomenon is called tenodesis. Current FES prostheses do not effectively take wrist position into consideration. Often times, adjusting the wrist position into flexion results in full finger extension when the muscle is stimulated. If finger extension is still lacking following the wrist angle adjustments, then a wrist/hand extension assist mechanism can be applied. Currently, there are no devices available that mechanically extend the wrist and hand while receiving electrical stimulation.

Electrode placement is an important issue for FES since the patient or their caretaker is required to set up the device each time they wish to use it. This involves ensuring that all electrodes are positioned accurately over the motor points of the muscles to be stimulated. Accurate electrode positioning ensures activation of the correct muscle without stimulation delivered to unwanted muscles. Many devices do not offer features that reliably position the electrodes in the correct location in a timely manner.

Thus, there is a continuing need for a neurological rehabilitation device that combines a functional neurological dynamic orthosis (wrist/hand assist or stretching) with electrical stimulation.

SUMMARY OF THE INVENTION

One embodiment of the present invention provides an orthotic device including a forearm support section that is configured to be releasably attached to a user's arm, a hand support section that is configured to be releasably attached to the user's hand, and an adjustable joint coupled to the forearm support section and the hand support section, wherein the joint allows the hand support section to move in a sagittal plane with respect to the forearm support section. At least one electromyography sensor is coupled to the forearm support section and positioned to sense activity of muscles in the user's arm, at least one electrode is coupled to the forearm support section and configured to provide electrical stimulation to muscles in the user's arm, and a controller is operatively coupled to the at least one electrode, the controller being configured to deliver electrical stimulation to the at least one electrode.

Another embodiment of the an orthotic device includes a forearm support section that is configured to be releasably attached to a user's arm, and a hand support section that is configured to be releasably attached to the user's hand. At least one electromyography sensor is coupled to the forearm support section and positioned to sense activity of muscles in the user's arm, at least one electrode is coupled to the forearm support section and configured to provide electrical stimulation to muscles in the user's arm, and a controller is operatively coupled to the at least one electrode, the controller being configured to deliver electrical stimulation to the at least one electrode. The at least one electromyography sensor senses activity in a first muscle group and the at least one electrode delivers electrical stimulation to a second muscle group.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, including the best mode thereof directed to one of ordinary skill in the art, is set forth in the specification, which refers to the appended figures, in which:

FIGS. 9A-9B are perspective views of a hand support section in accordance with one embodiment of the present invention for use with the neurological device of FIG. 4;

Figure 1:
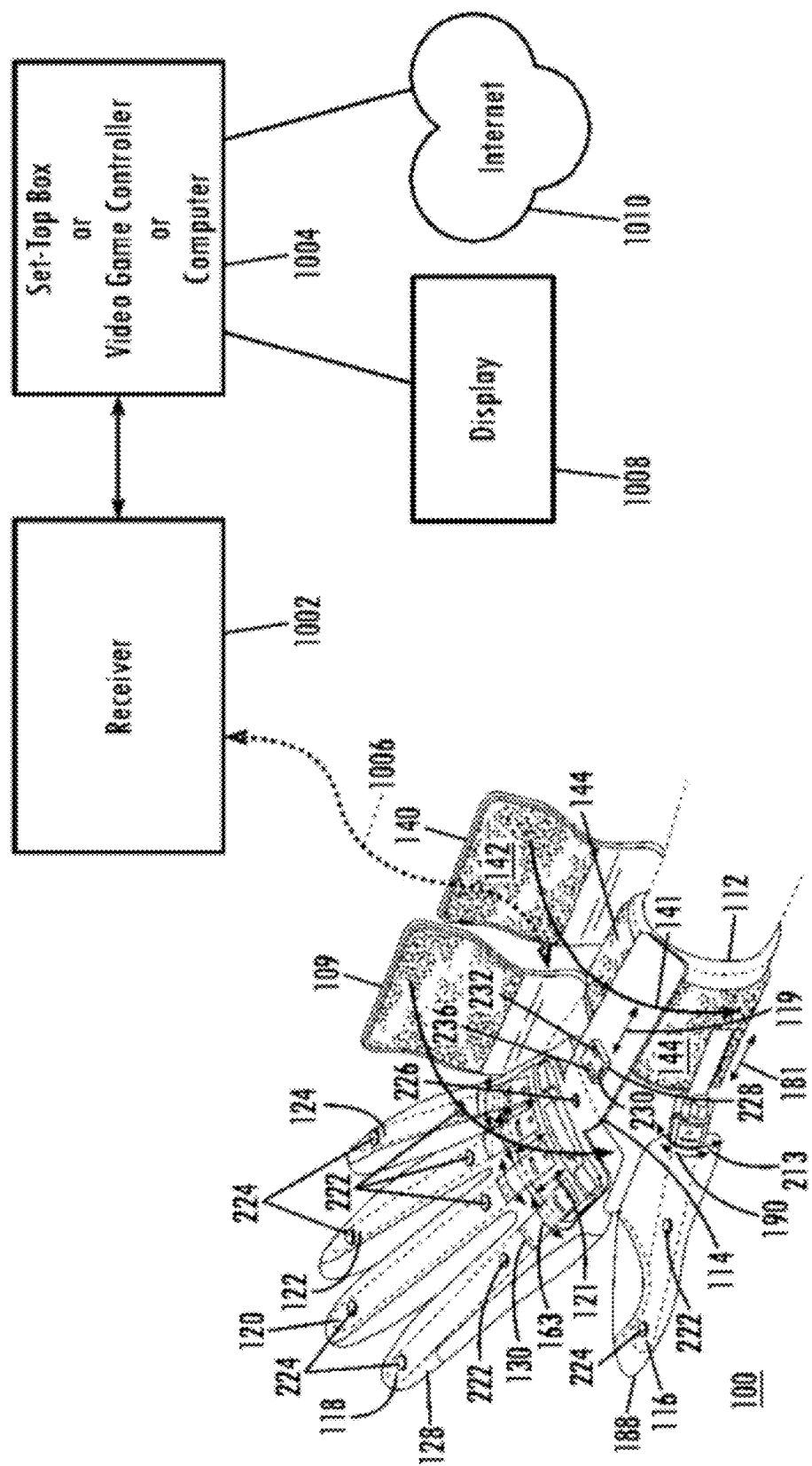
FIG. 1 is a perspective view of a prior art neurological device.

Repeat use of reference characters in the present specification and drawings is intended to represent same or analogous features or elements of the invention.

DETAILED DESCRIPTION OF THE INVENTION

One of ordinary skill in the art will understand that the present discussion is a description of exemplary embodiments only, and is not intended as limiting the broader aspects of the present invention. Various combinations and sub-combinations of the disclosed elements, as well as methods of utilizing same, which are discussed in detail below, provide other objects, features and aspects of the present invention. A repeat use of reference characters in the present specification and drawings represents the same or analogous features or elements of the invention.

Figure 2:
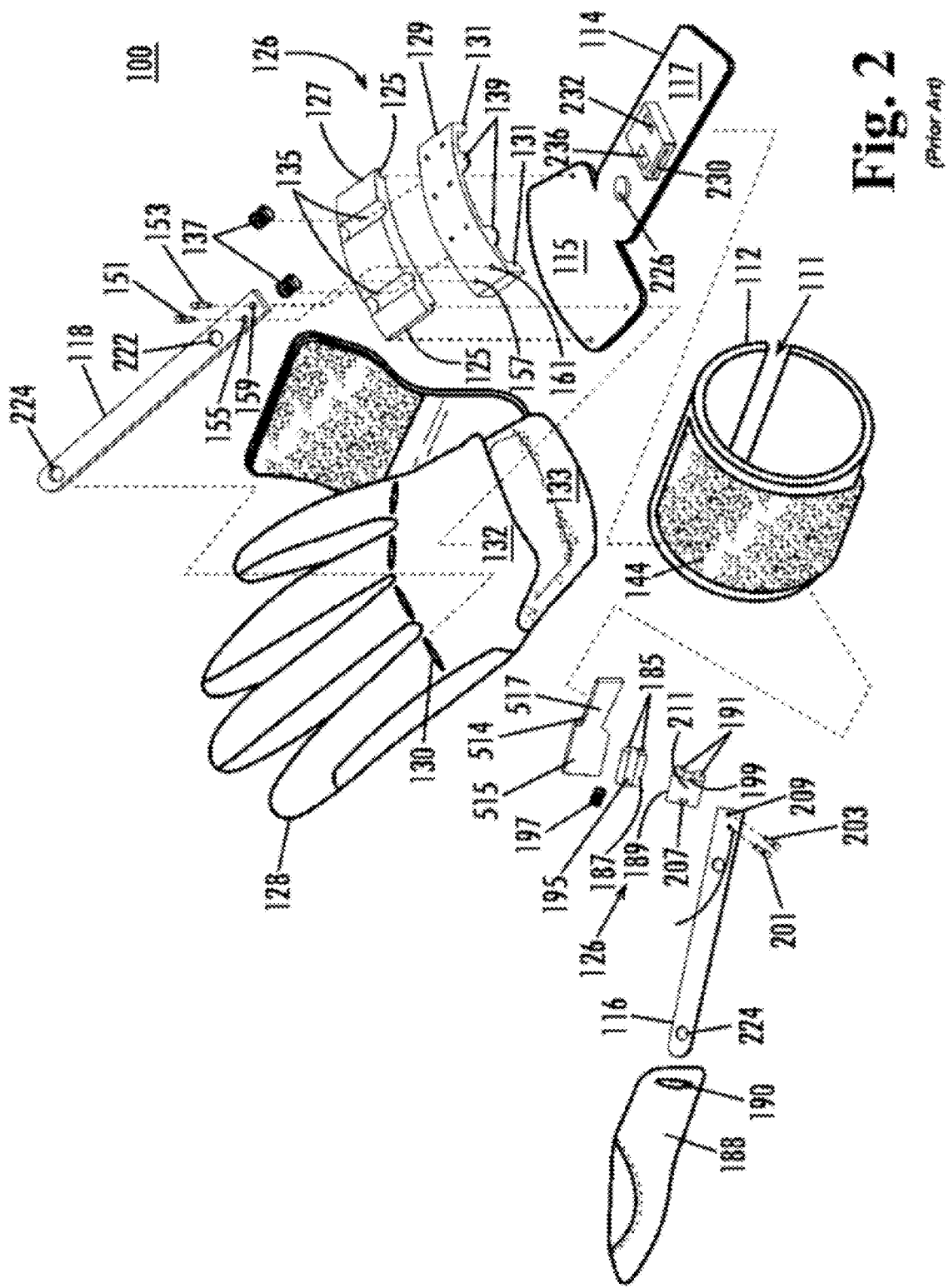
FIG. 2 is an exploded view of the prior art neurological device of FIG. 1.

Referring to FIGS. 1 and 2, a prior art neurological device 100 is shown having a forearm support section 112 and a hand support section 114 that are coupled together as described below. Forearm support section 112 is preferably formed from a flexible material such as plastic, metal, or alloy material. Forearm support section 112 also is configured and dimensioned to extend along a forearm of the user from the wrist rearwardly for a distance of at least several inches, and is generally tubular and designed to surround a portion of the wrist and forearm. Forearm support section 112 may be donned and doffed through an opening or slot 111 (FIG. 2) that extends the complete length of the forearm support section. Support section 112 is preferably lined with a permanent or removable close cell foam padded lining (not shown), and is adapted to tightly fit around the wrist and forearm with a frictional, interference fit. The lining may optionally include a non-skid material on the inner surface thereof to help prevent distal migration of forearm support section 112 along the user's arm. In one embodiment, forearm support section 112 is releasably secured on the user's forearm by an area of hooks 144 that is adapted to attach to an area of loops in conventional hook-and-loop attachment.

Hooks area 144 is preferably formed to substantially cover an outer surface of forearm support section 112 extending between the opposite ends that define slot 111. Hooks area 144 receives in hook-and-loop attachment areas of loops of a strap 140 (one such area 142 being shown in FIGS. 1 and 2). Strap 140 is preferably dimensioned and configured to extend substantially around forearm support section 112 to cover slot 111 and a base 117 (FIG. 2) of hand support section 114. Disposition of the covering attachment of strap 140 is illustrated by an arrow 141. To facilitate this, area 144 on forearm support section 112 is also adapted to receive, on a dorsum side thereof, a plurality of loops (not shown) disposed on an underside of hand support section 114 for removable attachment of base 117 to forearm support section 112. Additionally, area 144 is adapted to receive, on a radial side thereof, another plurality of loops (not shown), disposed on a thumb strut 116, for removeably attaching thumb strut 116 to forearm support section 112.

Hand support section 114 includes a platform 115, dimensioned and configured to extend between the radial side of the hand proximate the index finger across the back of the hand to little finger, and between the metacarpophalangeal joints and the carpals, i.e., between the base of the fingers and the wrist. Hand support section 114 further includes base 117 integrally formed with platform 115 and dimensioned and configured to extend across the length of forearm support section 112. Hand support section 114 preferably is constructed from a pliable, malleable material, e.g., a plastic or metal sheet that can be readily manipulated and shaped. That is, hand support section 114 preferably can be bent upward or downward at a juncture between platform 115 and base 117, as desired, to position the wrist at a selected one of a wide variety of angles when neurological device 100 is used to accommodate wrist flexion and/or extension. Thus, in use, hand support section 114 is preferably shaped so that the wrist is positioned upwardly as illustrated in FIG. 1.

A plurality of tension struts 118, 120, 122 and 124 are received in each respective finger of a glove 128 to provide tension between the fingers and hand support section 114. Each strut 118, 120, 122 and 124 is preferably constructed from, for example, spring steel and is formed with a thin or flat profile. Struts 118, 120, 122 and 124 are constructed to have varying degrees of resistance depending upon such factors as the thickness of the struts and materials from which the struts are made. Different resistances may be used with fingers having different characteristics of overall tone, tissue softness, and length. Each strut 118, 120, 122 and 124 corresponds in length and width to the finger to which it is attached. Suitable struts 118, 120, 122 and 124 may comprise, for example, thin resilient strips of about 0.01 to 0.008 inch stainless steel that is semi-rigid but nevertheless exhibits spring-like qualities.

Each strut 118, 120, 122 and 124 secured to a respective finger by inserting the strut in a respective elongate pocket 130 formed in each finger sleeve of glove 128. Each finger sleeve further is configured to enclose a respective one of the user's fingers, i.e., digit #2 through digit #5. Glove 128 includes a top surface 132 and a bottom portion 133. Each pocket 130 is preferably integrally formed in glove 128 during a conventional textile operation. Top surface 132 includes an area of loops (not shown) for attachment to an area of hooks (not shown) disposed on a bottom surface of platform 115. In should be understood that alternative attachment devices, such as snaps, buttons, zipper, buckles, etc. may be used to fasten the straps. In alternate constructions of glove 128, bottom surface 133 may be eliminated to provide an open palm construction.

Referring to FIG. 2, each strut 118, 120, 122 and 124 is releasably attached to hand support section 114, and specifically to platform 115, through an attachment mechanism 126 that is secured onto a top side of platform 115. Specifically, attachment mechanism 126 has a housing 127, which is secured to the platform top surface, and a slider 129, which mates with and slides, in directions designated by arrows 121 (FIG. 1), on top of housing 127. Slider 129 includes a C-shaped channel 131 on opposite sides that receive ledges 125 defined by housing 127, in interlocking engagement. Housing 127 further includes grooves 135 in which springs 137 are received and abut housing 127. Thus, when slider 129 is in interlocking engagement with the housing 127, one or more blocks 139, formed on an underside of slider 129, engage springs 137 and compress the springs when slider 129 moves away from base 117. Thus, springs 137 assist in opening the user's fingers by retracting the struts after the user makes a first or closes their hand.

Each strut 118, 120, 122 and 124 mounts to slider 129 by two fasteners, such as screws 151 and 153. A first screw 151 extends through a curved slot 155 formed in the respective strut and is received in mating engagement within a threaded bore 157 in slider 129. A second screw 153 extends through a circular opening 159 formed in a respective strut and is received in mating engagement within another threaded bore 161 in slider 129. In this configuration, each respective strut is capable of rotational movement, in a respective direction designated by arrows 163, about second screw 153, with first screw 151 acting as a stop to define the limits of rotation. Moreover, either screw 151 and 153 may be tightened to lock the strut in a particular orientation.

A strut 116 for attachment to the user's thumb preferably is constructed from, for example, spring steel and is formed to have a thin or flat profile. Suitable struts may comprise, for example, thin resilient strips of about 0.01 to 0.008 inch stainless steel that is semi-rigid. Thumb strut 116 has a length and width that corresponds to the length and width of the user's thumb. Attachment of strut 116 to a thumb sleeve is achieved by insertion of the strut into an elongated pocket 190 formed in thumb sleeve 128. Thumb sleeve 128 is configured to enclose the user's thumb, and pocket 190 is preferably integrally formed in the glove. Strut 116 is releasably attached to forearm support section 112 through a thumb support section 238 (FIG. 2) that, similar to hand support section 114, includes a platform 240 and a base 242. An attachment mechanism 186 is secured on a top surface of platform 240 and functions to movably mount strut 116 to platform 240.

Base 242 of thumb support section 238 includes an area of loops (not shown) on a bottom surface thereof for releasably engaging with hook area 144 on forearm support section 112. Thumb support section 238, and in particular base 242, is configured and dimensioned to include a bend proximate the carpals of the wrist, which allows the thumb support to be bent to various degrees of flexion and extension at the carpals to allow the thumb to be positioned in varying degrees of thumb abduction, adduction, and opposition, depending on where attachment mechanism 186 is attached to thumb support section 238.

Referring again to FIG. 2, a slider 189 mates with and slides, in a direction designated by arrow 181 (FIG. 1), on top of housing 187. Slider 189 includes a C-shaped channel 191 on opposite sides thereof that receive side ledges 185, formed on housing 187, in interlocking engagement, in a similar manner to housing 127 and slider 129, as discussed above. Housing 187 further includes a groove 195 in which a spring 197 is received, which abuts housing 187 and, when slider 189 is in interlocking engagement with housing 187, a block 199 of slider 189 engages spring 197 and compresses it when slider 189 moves in a direction toward the thumb sleeve 188. Compression occurs when strut 116 is extended during closing of the hand, and spring 197 assists in opening of the hand by urging retraction of strut 116 and extension of the thumb.

Strut 116 is mounted to slider 189 by two fasteners, for example, screws 201 and 203. First screw 201 extends through a curved slot 205 formed in strut 116 and is received in mating engagement within a threaded bore 207. Second screw 203 extends through a circular opening 209 formed in strut 116 and is received in mating engagement within a threaded bore 211 in slider 189. In this configuration, strut 116 is capable of rotational movement, in the direction designated by arrow 213, about second screw 203, with first screw 201 acting as a stop defining the limits of such rotation.

A data device 228 is mounted on hand support section base 117 and comprises a processor (not shown), memory (not shown), a receiver (not shown), a transmitter (not shown), a secure digital (SD) slot 230, a USB port 232 and an antenna 236. Data device 228 communicates with a plurality of sensors 222, 224 and 226 located on neurological device 100. In particular, sensor 226 is positioned on hand support section 114 proximate data device 228 and may act as a reference for the other sensors. For each finger, sensors 222 are positioned proximate the proximal phalanxes, intermediate the user's knuckles and their proximal interphalangeal joints. Sensors 224 are positioned proximate to the user's distal phalanxes, intermediate the distal interphalangeal joints and the tips of the fingers. Sensors 222 may be coupled to glove 128 or attached to each respective strut 118, 120, 122, 124 and 116, as shown in FIGS. 1 and 2. With regard to the thumb, sensor 222 is positioned proximate the proximal phalanx, intermediate the knuckle and the distal interphalangeal joint. Sensor 224 is positioned proximate to the distal phalanx, intermediate the distal interphalangeal joint and the tip of the thumb. Similar to the finger sensors, the thumb sensors may be coupled to the thumb sleeve or directly attached to thumb strut 116, as shown in the figures.

It will be apparent to those skilled in the art that sensors 222, 224 and 226 may generate short range radio signals, which may be processed in accordance with public or proprietary processing circuitry and/or software. For example, communication of radio signals can be carried out using standards such as BLUETOOTH or other suitable wireless technology (e.g., such as IEEE 802.11). While it is preferred to employ technology not requiring line of sight, the embodiments described herein can be applied to technologies requiring line of sight such as infrared signals. Sensors 222, 224 and 226 may also be hardwired directly to data device 228. In either configuration, the sensors may contain one or more of a passive or active transceiver, accelerometers, strain gauges, pressure sensors, optical readers, potentiometers, etc. for detecting the movement of the sensors and the force applied to each sensor by the user.

The sensors are configured to detect the orientation of the fingers and thumb with respect to the user's palm, the speed the fingers move relative to one another and the user's hand and the pressure exerted by each finger on a real or virtual object. It is also contemplated that the sensors, or additional sensors distributed throughout the glove can provide tactile feedback to the user's fingers and thumbs to simulate the tactile feel of an object that the user is grasping in a virtual reality program.

In use, forearm support section 112 is first positioned and secured on the user's forearm, and hand support section 114 is shaped as desired to position the user's wrist relative to the forearm. In this respect, a healthcare worker, the user, or another person may bend hand support section 114 to achieve the desired angle for positioning of the wrist. Hand support section 114 is positioned or repositioned along the direction of arrows 119 on forearm support section 112 such that the bend in hand support section 114 is proximate to the user's wrist. A strap 109 may be fastened over the ends of struts 118, 120, 122 and 124 and attachment mechanism 126 for covering thereof. In this configuration, strap 109 includes an area of loops (not shown) for engagement with areas of hooks (not shown) formed on top surface 132. Thumb strut 116 is shaped and manipulated to position the thumb relative to forearm support section 112, and is attached to platform 240 of thumb support section 238. A strap 142 extends over and covers base 242 of thumb support section 238 including attachment mechanism 186 in its disposition on forearm support section 112.

Once attached, neurological device 100 creates rearwardly-directed forces that urge the fingers and thumb into an open hand position in which the fingers and thumb are extended. The resistance provided by each of the digit tensioners, i.e., each of tension struts 116, 118, 120, 122 and 124 is not so great as to prevent the user from moving their fingers and thumb towards a gripping position, thereby allowing the wearer to exercise (and rehabilitate) the hand. Neurological device 100 will generally position the user's wrist into extension with the digits extended, whereby the wearer will be in a position to grasp an object and, after grasping of the object, tension struts 116, 118, 120, 122 and 124 will assist in reopening the digits so the user will once again be in a position to grasp an object. Furthermore, each of the struts 116, 118, 120, 122 and 124 may be replaced by struts of different degrees of resilience, whereby the healthcare worker, the wearer, or another person can continue to select struts with the desired resistance for each digit as the healing and rejuvenation process progresses.

During rehabilitation, compliance and progress data is of great importance for ensuring compliance with the rehabilitation plan and shaping the rehabilitation process. To assist with compliance and rehabilitation planning, data device 228 is programmed to record the date, the start time and the end time for each occurrence that device is used. Data device 228 is also programmed to record all sensor data, and calculate progress and compliance data such as the number of times the user's hand is opened and closed, the range of motion and speed of each finger and thumb and the closing pressure exerted by the user's fingers when the fingers and thumb are moved into a grasping position. In this manner, a healthcare provider can use this information to determine both progress and compliance by the user.

Compliance information and progress information may be transmitted by data device 228 either wirelessly or via a wired connection 1006 to a receiver 1002 that is connected to a computing device 1004. Captured data can be manually or automatically transmitted via an internet connection 1010 from the computing device to the healthcare provider. In some embodiments, data device 228 may have its own designated IP address to allow the device to transmit the data over a wireless internet connection directly to the healthcare provider. In other embodiments, progress and compliance data may be transferred by way of an SD card received in SD slot 230 or by a USB connection through USB port 232. In all cases, the repetition data, range of motion data and closing pressure for each finger and thumb is transmitted to the healthcare provider to assist in providing a comprehensive up-to-date rehabilitation plan, as well as to support insurance billing through compliance data.

In addition to collecting rehabilitation progress and compliance data, data device 228 may also be configured to work interactively with computing device 1004 so as to function as a data input device. In this manner, a user of neurological device 100 can move their hand, wrist and fingers so that sensors 222 and 224 provide input signals that correspond to movement of the user's hand. Computing device 1004 is in communication with a display monitor 1010 so that the computing device transmits digital data to display 1010 to be viewed. Display 1010 may display text, menus and/or graphics, which show a virtual hand moving on the screen in relation to the user's movements, text indicating progress data or both. In particular, each of sensors 222 and 224 are configured to generate commands in response to a user's hand movements that are captured by data device 228 and transmitted to computing device 1004 through receiver 1002. The captured digital data enables neurological device 100 to be used as an interactive device with a computer program executed by computing device 1004. Thus, movement of a particular finger or fingers is transferred to computing device 1004 to initiate a command, response to a query, maneuver objects in an interactive video game, etc. Thus, the user can reach for and grasp virtual objects to assist in their rehabilitation without having to actually pick up or hold a physical object, which may be dangerous or difficult when the user lives alone or is home alone during a rehabilitation session. Use of neurological device 100 in conjunction with a virtual reality program or game also encourages the user to engage in rehabilitation exercises compared to just sitting and opening and closing their hand and fingers without interacting with a physical or virtual object.

Figure 3:
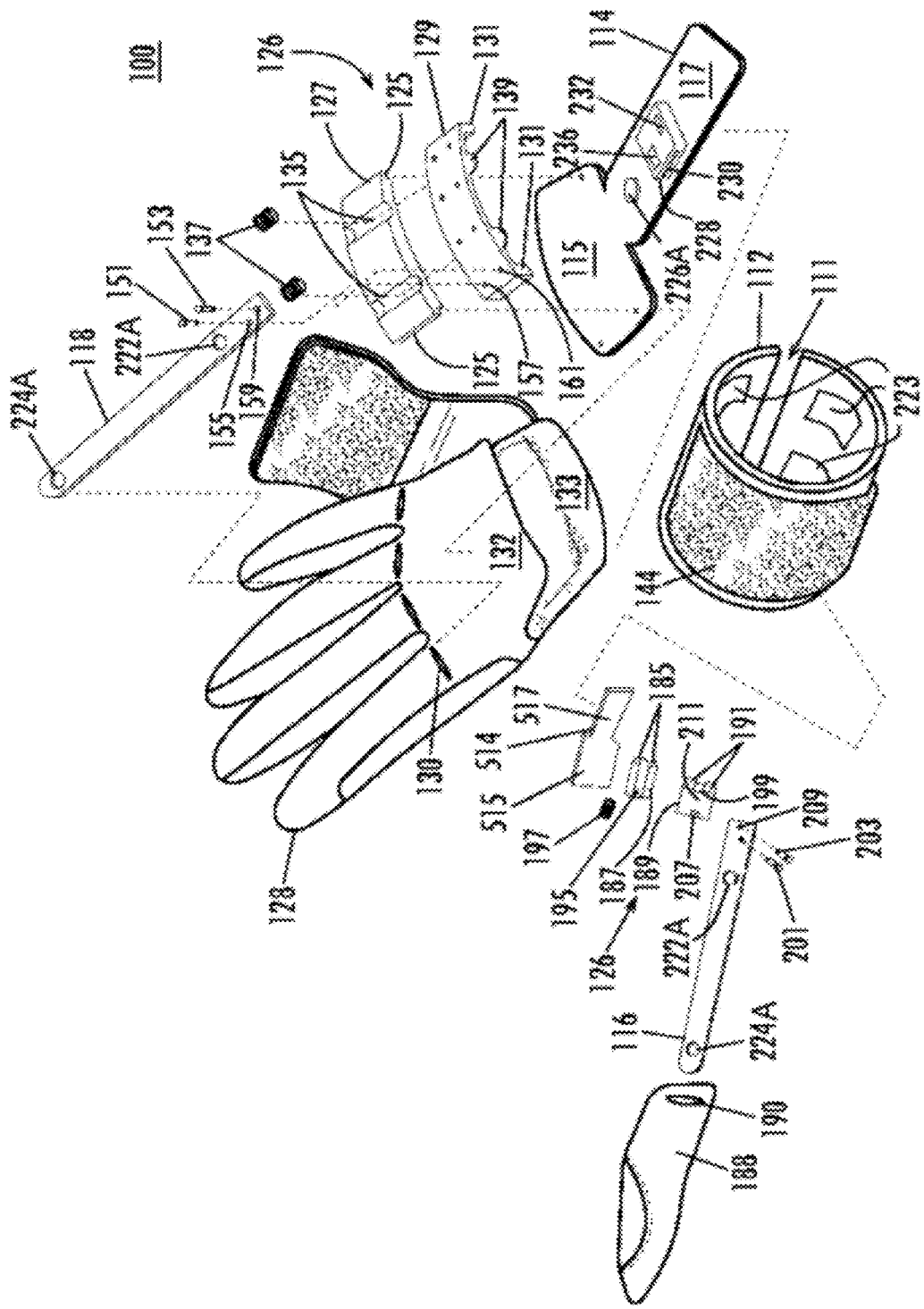
FIG. 3 is an exploded perspective view of a neurological device in accordance with one embodiment of the present invention.

Referring to FIG. 3, one embodiment of the present invention is illustrated having mechanical finger assist in combination with biofeedback. In general, the design of the mechanical finger assist orthotic of FIG. 3 is somewhat similar to that described in FIGS. 1 and 2. Therefore, only the differences will be discussed herein. In one preferred embodiment, sensors 222 and 224 are replaced with haptic feedback electrodes 222A and 224A that provide vibratory sensations to the user's fingers when triggered. Haptic feedback technology uses tactile feedback that takes advantage of a user's sense of touch by applying forces, vibrations, and/or motions to the user. This mechanical stimulation may be used for controlling virtual objects and to notify the user when specific muscle contraction has exceeded a predetermined value. Additionally, electromyography (EMG) sensors 223 are placed in forearm support section 112 and are operatively coupled to data device 228 and haptic feedback electrodes 222A and 224A.

Thus, when EMG sensors 223 detect a predetermined level of muscle activity in the user's forearm muscles, data device 228 triggers haptic feedback sensors 222A and 224A to provide tactile feedback to the user. In addition to haptic feedback sensors 222A and 224A, data device 228 may also provide visual and auditory feedback to provide the user with a sense of how they are progressing with contraction/relaxation of the flexor and extensor muscles. Such feedback may be in the form of lights, sounds or a combination of both. The feedback can also be used with virtual reality programs to provide the user tactile feedback when grasping and releasing virtual objects. It should be understood to those of skill in the art that the haptic, auditory and visual feedback can be combined with the sensor and data capture technology shown in the prior art of FIGS. 1 and 2 to provide an enhanced user experience. That is, in addition to biofeedback, the device may also be configured to capture user information during rehabilitation, where the captured data is relayed back to a caregiver so that rehabilitation progress may be monitored.

It should be understood that the EMG sensors and the haptic feedback sensors may be positioned at the finger tensioner mechanisms, the hand support section and the forearm support section. Thus, sensing may occur at any one of the finger, hand, wrist and forearm and biofeedback may be delivered to one or more of these areas as well.

Figure 4:
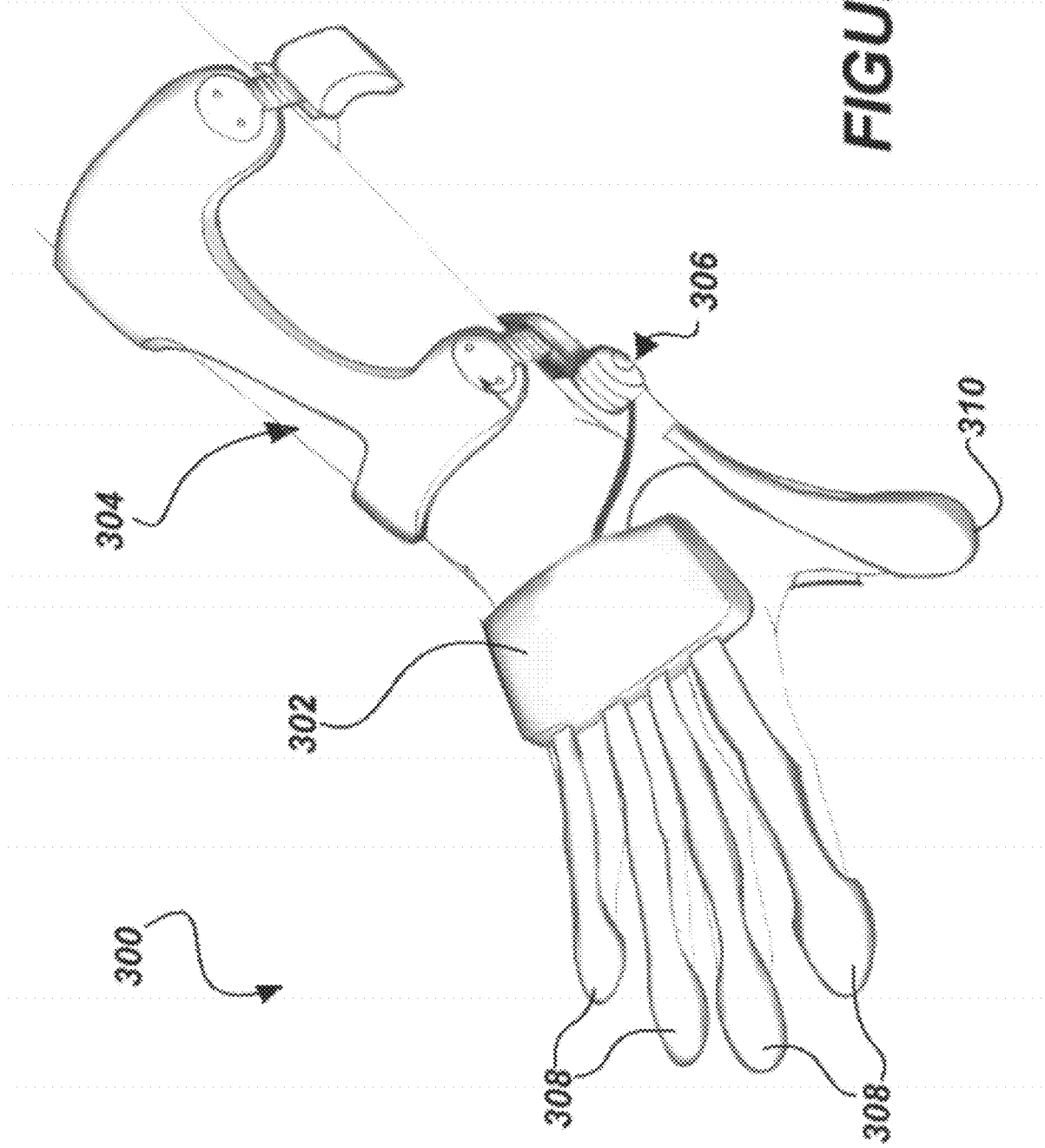
FIG. 4 is a perspective view of a neurological device in accordance with one embodiment of the present invention.

Referring to FIG. 4, a mechanical finger assist orthotic 300 according to one embodiment of the present invention is shown having a hand support section 302, a forearm support section 304 coupled to the hand support section by a pivoting joint 306, a plurality adjustable finger assists mechanisms 308 and a thumb assist mechanism 310. Hand support section 302, finger assists mechanism 308 and thumb assist mechanism 310 function to perform mechanical finger assist for moving the user's fingers from a position of flexion to extension and are discussed in greater detail herein. It should be understood that pivoting joint 306 may be unilaterally positioned on the radial or ulna side of the wrist, or it may be configured to be bilateral.

Figure 5:
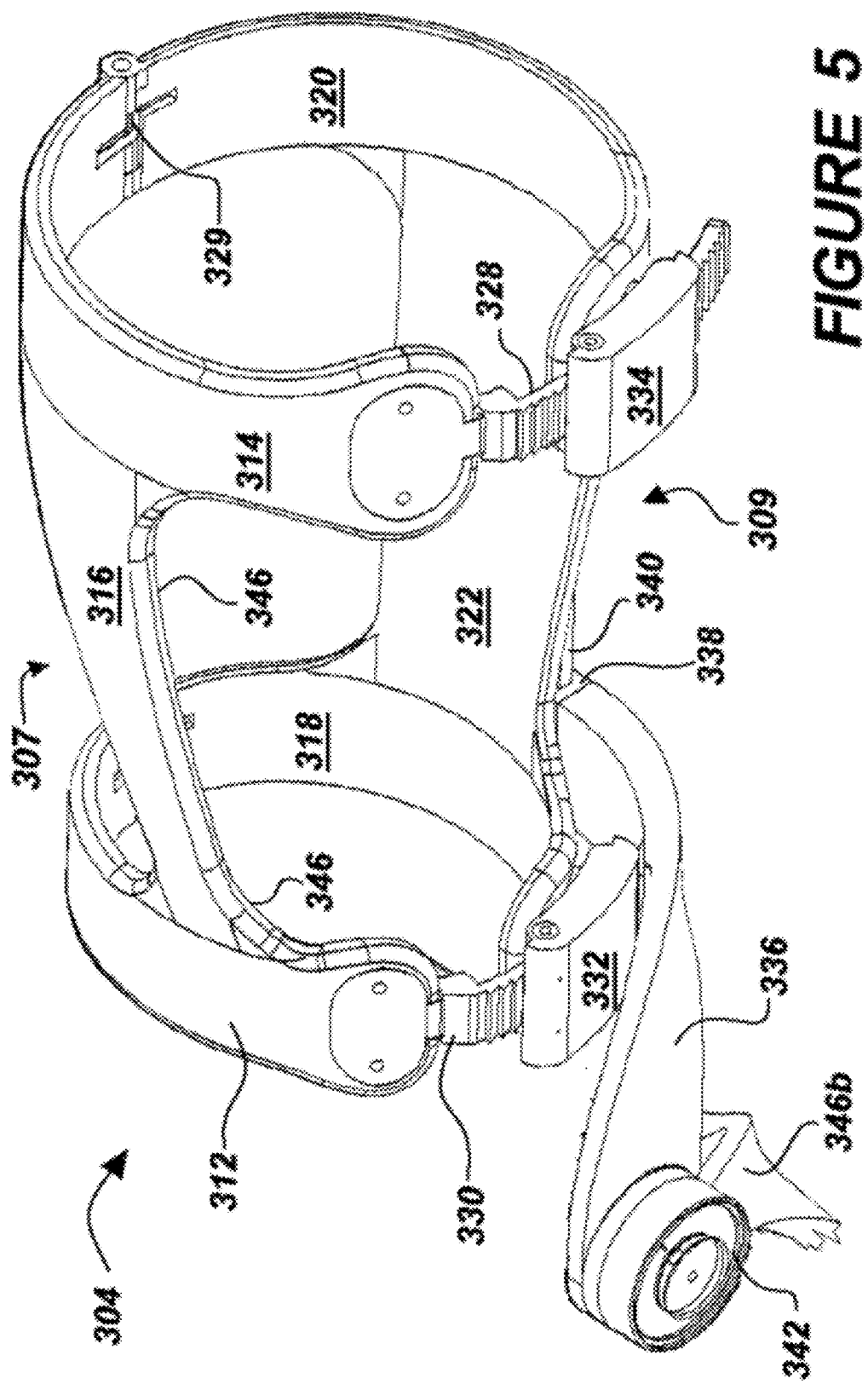
FIG. 5 is a perspective view of a forearm support device in accordance with one embodiment of the present invention for use with the neurological device shown in FIGS. 3 and 4.

Referring to FIG. 5, forearm support section 304 of FIG. 4 is shown having a first half 307 that is positioned adjacent the dorsum side of the forearm and a second half 309 that is positioned adjacent the volar side of the forearm. Forearm support section first half 307 defines first and second semicircular cuff portions 312 and 314 and a cross member 316. Forearm support section second half 309 defines first and second semicircular cuff portions 318 and 320 and a cross member 322. It should be understood that in some embodiments, only one of cross members 316 and 322 may be used. First half first semicircular cuff portion 312 is pivotally coupled to second half first semicircular cuff portion 318 by a first pivotal connection 324, and first half second semicircular cuff portion 314 is pivotally coupled to second half second semicircular cuff portion 320 by a second pivotal connection 326. The pivotal connections may be a hinge type connection, a ball and joint type connection or any other suitable connection that allows forearm support section first half 307 to move relative to forearm support section second half 309. Springs (only one shown in FIG. 5) 329 bias forearm support section first half 307 apart from forearm support section second half 309 to assist in donning the forearm support.

Ratchets straps 328 and 330 are respectively coupled to first half first semicircular cuff portion 312 and first half second semicircular cuff portion 314. The ratchet straps may be fixedly coupled to the first half, pivotally coupled to coupled in any other suitable matter that enhances operation. Ratchet covers 332 and 334 are respectively pivotally coupled to second half first semicircular cuff portion 318 and second half second semicircular cuff portion 320. Ratchet covers 332 and 334 are configured to each receive a respective ratchet strap 328 and 330 to releasably secure forearm support section 304 on the user's arm. It should be understood that any type of closing mechanism may be used in place of ratchet straps 328 and 330 and ratchet covers 332 and 334, for example, hook and loop straps, etc.

The ratchet straps and covers allow the user to easily secure the forearm support section on the arm by initially placing the ratchet straps into its respective ratchet cover, positioning the forearm support section at the proper position and squeezing the first and second half portions together forcing the ratchet strap through the ratchet cover. Cross members 316 and 322 are formed as flexible members that allow for unique tightening of first half first semicircular cuff portion 312 and second half first semicircular cuff portion 318 independent of first half second semicircular cuff portion 314 and second half second semicircular cuff portion 320. That is, as ratchet strap 328 is pushed through ratchet cover 332, the action does not affect the position of ratchet strap 330 in ratchet cover 334. Thus, as a result, more even pressure distribution on the user's arm is achieved. A padding layer 346 further provides for even distribution of pressure between the orthotic and the user's arm, in addition to closing the gaps between the orthotic and the user's arm.

A hinge bar 336 has a first end 338 that is slideably coupled to a slide bar 340 and a second end that terminates into joint 306. Joint 306, in one preferred embodiment is formed by a wrist hinge 342 having four present angle positions of −15 degrees, 0 degrees, 15 degrees and 35 degrees. In other preferred embodiments, the wrist hinge 342 can be adjusted in increments one or more degrees. In other preferred embodiments, in addition to the preset angles, wrist hinge 342 can be unlocked so that the hinge is fully moveable. In still other preferred embodiments, wrist hinge 342 may be set so that the hinge allows the user to move their wrist into extension but is locked to prevent the wrist from moving when it is in flexion. Finally, in any of these embodiments, wrist hinge 342 may be spring biased against flexion and extension so that when the hinge is locked into position, the hand support section may still move over a predetermined angle with respect to the forearm support section to provide comfort for the user during use.

Slide bar 340 contains a stopper (FIG. 12) 344 that prevents hinge bar first end 338 from sliding off of slide bar 340. Hinge bar first end contains two inwardly pointing flanges (not shown) that are slideably received in respective channels 340a defined by slide bar 340. The sliding action between hinge bar 336 and forearm support section 304 allows for the hand section 302 (FIG. 4) to move linearly with respect to forearm section 304 when the orthotic is in use. That is, as a user moves their wrist from an extension position into a flexion position, the hand moves relative to the forearm causing hand support section 302 (FIG. 4) to move relative to forearm support section 304. The sliding connection between slide bar 340 and hinge bar 336 allows the hand support section to move in a sagittal plane with respect to the forearm support section to adjust for the relative movement. In addition to the sagittal movement, wrist hinge 342 also allow for pivotal movement. Thus, the design of orthotic 300 allows the user's hand and arm to move along the natural paths during flexion and extension of the fingers and wrist during rehabilitation.

Figure 6:
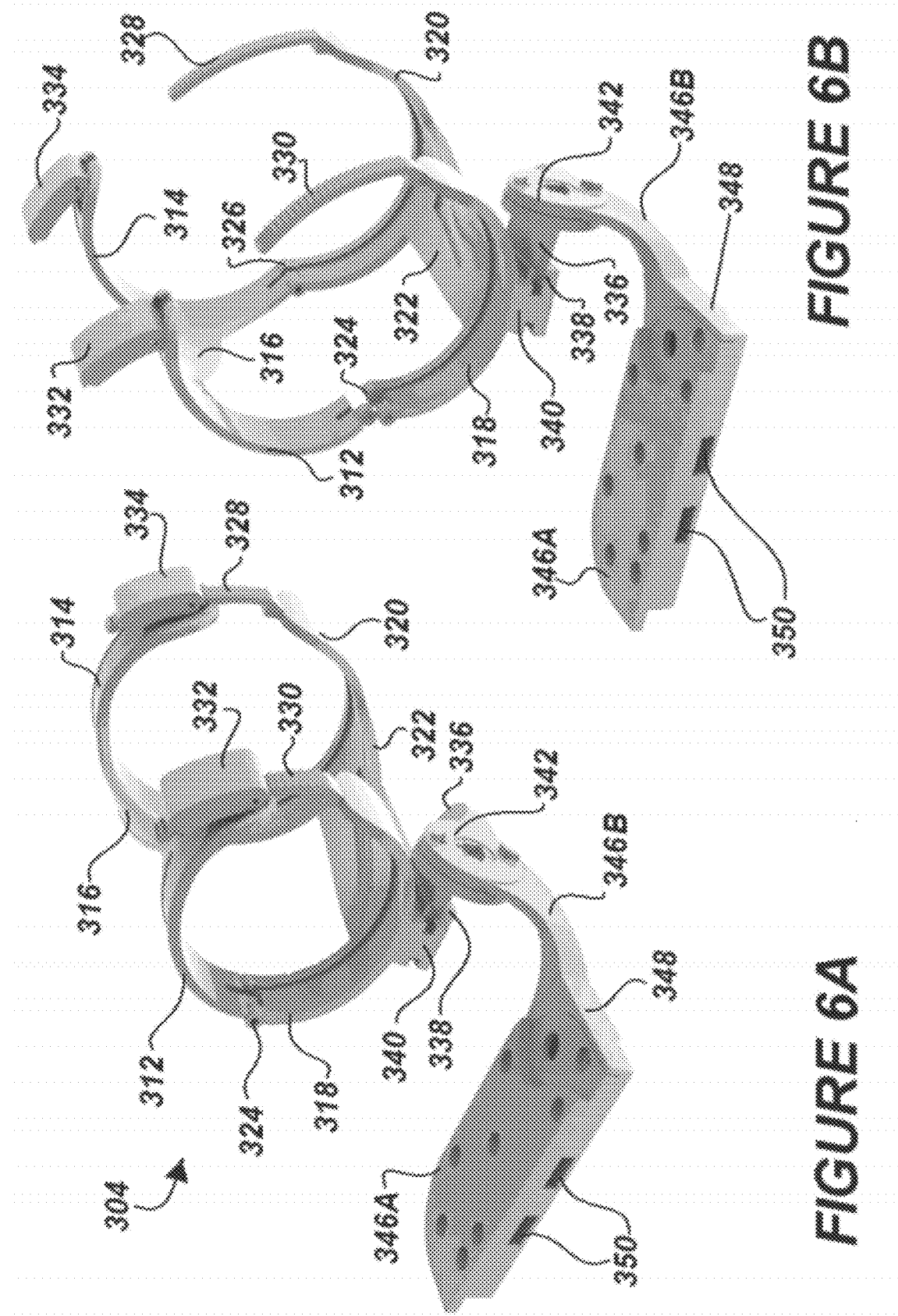
FIGS. 6A and 6B are perspective views of another embodiment of a neurological device of the present invention.

Referring to FIGS. 6A and 6B, a contracture orthotic 304 is shown having a hand section 348 with a first end 346A adapted to receive various hand plates (discussed below) and a second end 346b that terminates at wrist hinge 342. Wrist hinge 342 allows for hand section 348 to be disposed at various angles with respect to forearm section 304 as described above. In one preferred embodiment, hinge 342 is an indexed pivot point that allows a user to easily change the angle between the hand section and the forearm section by depressing the outside surface of hinge 342, which moves a detent out of engagement with ratchet teeth formed in the hinge. In other embodiments, other types of hinge joints may be used, for example, a nut and screw may be used to lock the joint in position. It should be understood that the indexing joint of FIGS. 6A and 6B are shown for illustrative purposes and should not limit the scope of the various types of joints that come within the scope of the present invention.

Figure 7:
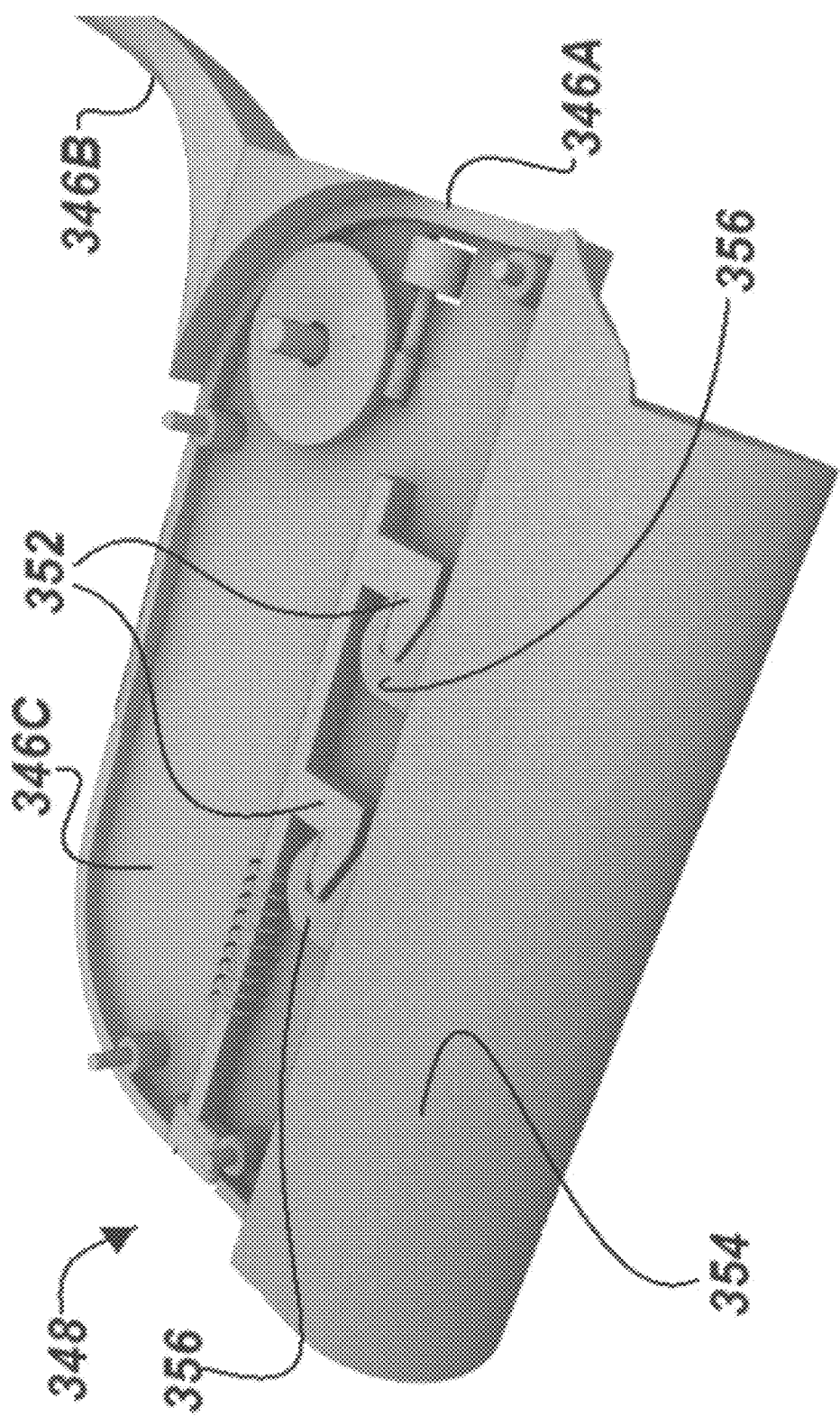
FIG. 7 is a partial perspective view of a hand piece in accordance with one embodiment of the present invention for use with the neurological device of FIGS. 6A-6B.
Figure 8:
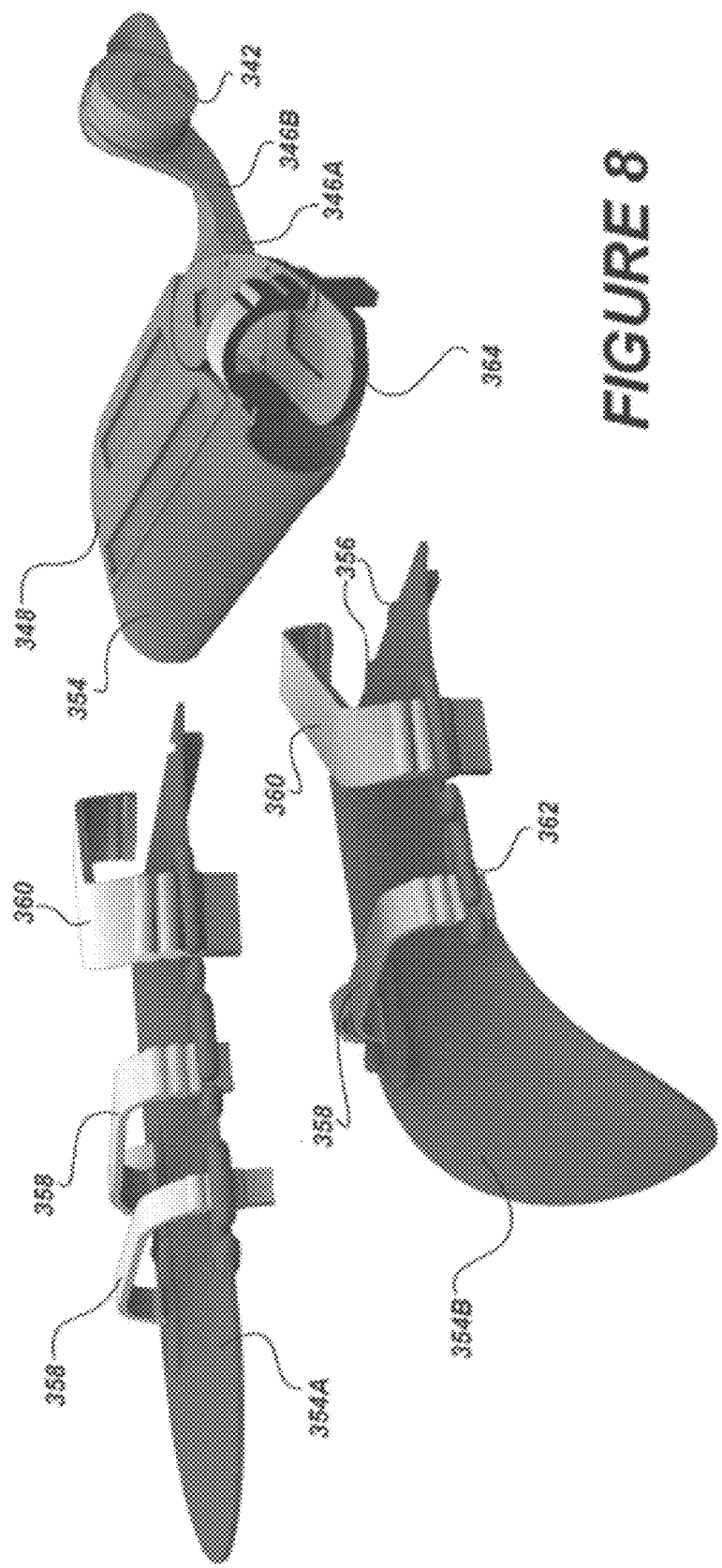
FIG. 8 is a perspective view of various embodiments of hand plates for use with the neurological device of FIGS. 6A-6B.

Referring to FIG. 7, hand section 348 is shown having an internal cavity 346C. Two locking flanges 352 are positioned opposite respective openings 350 (FIGS. 6A and 6B). Locking flanges 352 are configured to receive and lock against opposing flanges 356 formed on the various hand plates that may be attached to hand section 348. Referring to FIG. 8, various hand plates 354. 354A and 354B are shown configured for attachment to hand piece 348. Depending on the amount of contracture or hypertonicity the patient exhibits, the clinician will decide which hand plate to select. For example, if the patient demonstrates increased contracture and tone, then a smaller diameter hand plate 354 would be used. Conversely, if the patient demonstrates mild tightness and tone in the hand, then a larger diameter hand plate 354B or flat hand plate 354A would be used. The smaller the diameter hand plate, the less of a stretch provided. The larger the diameter hand plate, the greater the stretch provided. Finally, flat hand plate 354A will provide the most stretch to the long finger flexors.

In particular, first interchangeable hand plate 354 consists of a handle bar that is cylindrical in shape with a padding exterior skin formed thereon. The handle bar frame may be formed from injection molded ABS or spring steel and the padded exterior skin may be formed from molded urethane. A thumb rest 364 may be attached to handpiece 348 either through a stationary attachment or through a pivotal attachment where the position of the thumb rest may be moved according to the user's needs. Second interchangeable hand plate 354B is shown having a C-shaped base plate formed from, for example, die cut spring steel. An exterior padding skin is formed from molded urethane and strap mounts and locks are formed from over molded TPE. Finger straps 358 are positioned across the width of the hand plate so as to retain the fingers adjacent to the hand plate. Moreover. A hand strap 360 maintains the placement of the volar part of the user's hand against handpiece 348 and the back end of hand plate 354B.

Still referring to FIG. 8, a third 354A is a flat hand plate formed from, for example, die cut spring steel. Strap mounts and locks 362 are formed from over molded TPE and an exterior padding skin is formed from molded urethane. However, it should be understood that the exterior padding skin may be formed from any suitable material. (it can be any material as well) Finger straps 358 are positioned across the width of the hand plate so as to retain the fingers adjacent to the hand plate. Moreover. A hand strap 360 maintains the placement of the volar part of the user's hand against handpiece 348 and the back end of hand plate 354A.

In each of the embodiments of hand plates described above, locking flanges 356 are located at one end to connect the hand plate to handpiece 348. It should be understood that in each of the hand plates, the exterior padding skin may be permanently attached to the spring steel hand plate or it may be releasably attached to the hand plate using any suitable connector, for example hook and loop. Moreover, other connecting structures may be used to secure the hand plate to the handpiece, for example, Velcro straps, snaps, screws, etc.

Referring to FIGS. 9A and 9B and back to FIG. 4, one embodiment of a hand support section 302 is shown that allows for the adjustment of tension provided by each finger tension mechanism 308. Hand support section 302 contains a housing 366 a tension knob 368 and a plurality of engagement switches 370 located on a top surface therein. A plurality of openings 372 are formed in a front of housing 366 where one end of finger tensioner mechanism 308 is operatively coupled to hand support section 302. It should be understood that while housing 366 is shown to have sharp edges and angles, in some embodiments, the edges may be rounded and the surfaces may be contoured to better rest against the user's dorsum surface of their hand. Moreover, housing 366 have an exterior padding layer of covering formed from a polymer, elastomer or any other suitable material. Also, a thumb mechanism (FIG. 4) may be operatively coupled to housing 366 using ball and joint type connection or any other suitable connection.

Figure 10:
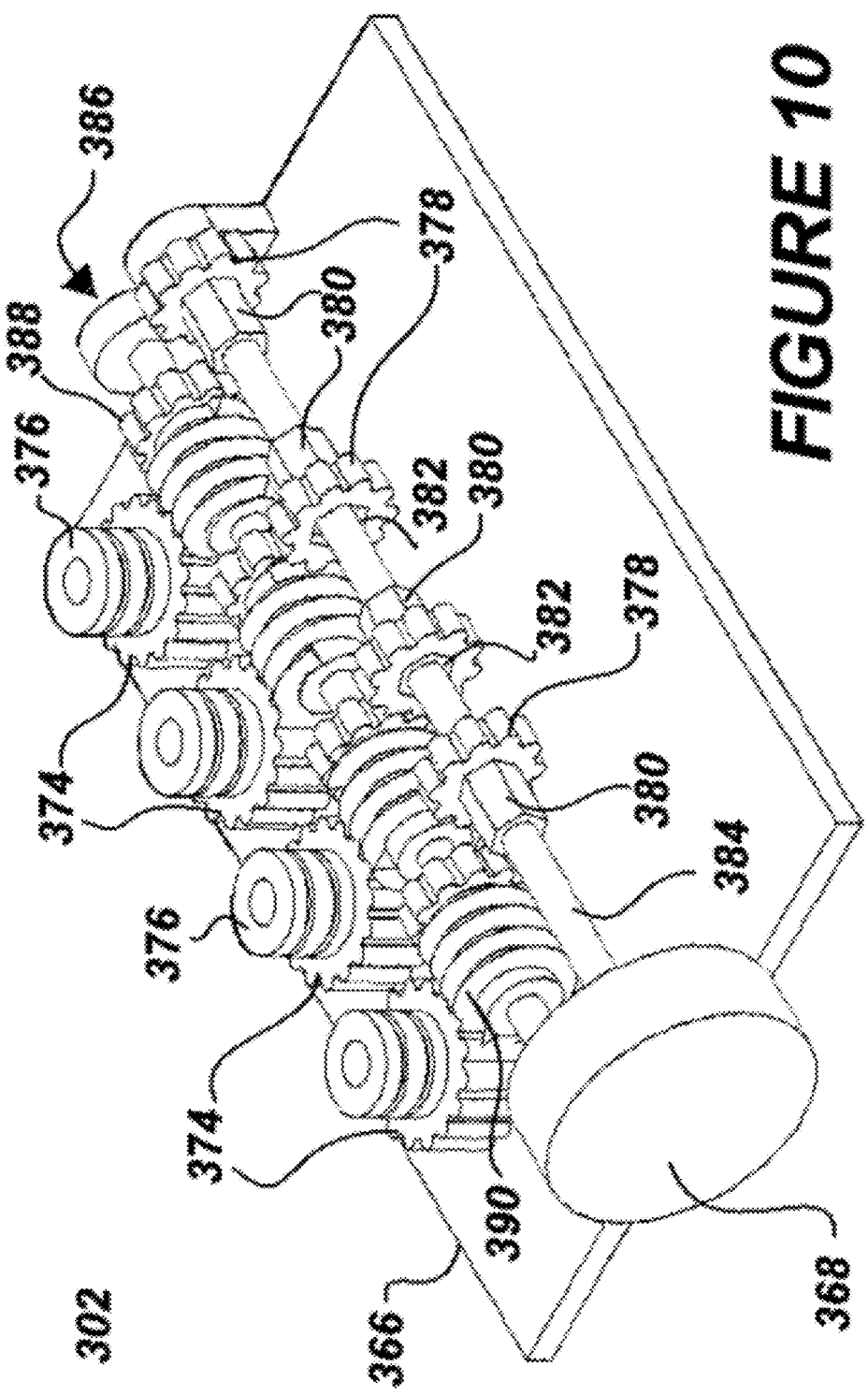
FIG. 10 is partial perspective view of the hand support section of FIGS. 9A-9B.
Figure 11B:
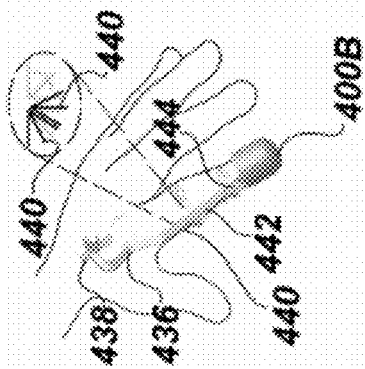
FIGS. 11A-11E are perspective views of various embodiments of a finger tension mechanism for use with the neurological device of FIG. 4.

Referring to FIG. 10, the internal structure of hand piece 302 is shown having a rod 384 coupled to tension knob 368. A plurality of gears 378 are rotatably received on rod 384 and are moveable between a first position where the gears rotate with respect to the rod and a second position where the gears are rotatably fixed on the rod through the interconnection of a locking lug 380 and shaped bore 382. Each of gears 378 are operatively coupled to a respective switch 370 (FIGS. 9A and 9B) so that movement of the switch moves the gear between the first and second positions. A coupling mechanism 386 is formed from a plurality of gears 388 and a plurality of worm gears 390 that are rotationally and axially fixed to a rod (not numbered). Gears 388 engage with gears 378 when gears 378 are in the second position. Worm gears 390 are in operative engagement with a respective spindle gear 374, which are operatively coupled to respective spindles 376. Spindles 376 are configured to receive a tension rope or cable around the spindle so that when spindle gear 374 rotates, the rope or cable (not shown) is taken up or released from the spindle depending on whether tension is to be increased or decreased in the individual finger tension mechanisms 308. The rope or cable (not shown) may be operatively coupled to finger tension mechanisms 308 to increase or decrease the amount of tension that is exerted against the user's fingers, as shown in FIGS. 11A-11B. In one preferred embodiment, each rope or cable would include an extension spring in-line with the rope or cable. In other preferred embodiments, a torsion spring (not shown) is operatively coupled to spindle 376.

Figure 11C:
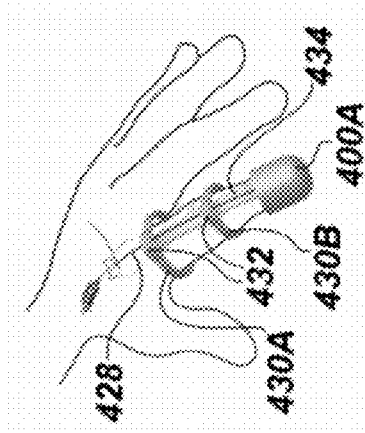
Figure 11A:
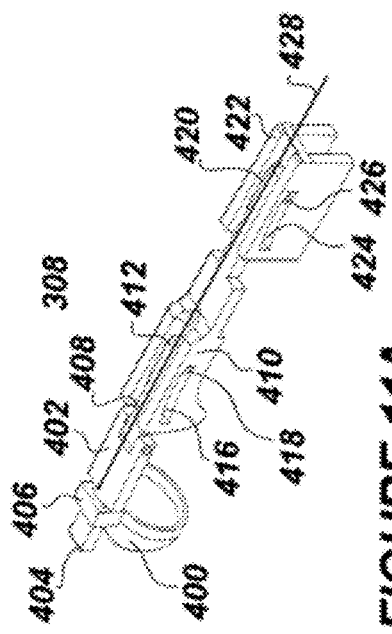

Referring to FIGS. 11A-11C, various embodiments of finger tensioners are illustrated. In particular and referring to FIG. 11A, a tensioner mechanism is shown for use with the hand support section 302 of FIGS. 9A-10). The tensioner has a finger cap 400 that is slideably coupled to a first end 404 of a distal phalange plate 402 by a slide box 406. A distal interphalangeal hinge is formed by a second end of distal phalange plate 402, which is pivotally coupled to a middle phalange plate 408. Middle phalange plate 408 is pivotally coupled to a proximal phalange plate 410 at a first second end 412 through a pin 418 and arched slot 416, which together form a traveling hinge. A second end 420 of proximal phalange plate 410 is pivotally coupled to a metacarpal plate 422 via a pin 426 and arched slot 424, which together form a traveling hinge. A cable 428 is coupled at one end to one of the phalange plates (shown coupled to the distal phalange plate 402) and at a second end to hand piece spindle 376 (FIG. 10). Guide rails (not shown)

are positioned proximate each traveling hinge to guide the motion of the respective phalange plate to ensure proper finger motion is allowed.

Referring to FIG. 11B, a second embodiment of a finger tensioner is shown having a finger cap 400 moveably coupled to a flexible longitudinal spine 434. Additionally, a plurality of support uprights 430A and 430B are rigidly coupled to flexible longitudinal spine 434 so that each upright does not move relative to the spine. Spine 434 may be formed from various suitable polymers and elastomers, or some combination thereof. When a finger is moved into flexion, uprights 430A and 430B become spaced apart as the spine flexes, while a tension cable 428 provides restoring force. Tension cable 428 may be coupled to handpiece spindle 376 (FIG. 10) similar to the previous embodiment. Loops 432 formed on each upright act as guides for tension cable 428, and also act as anchor points so that the restoring force at each knuckle can be adjusted.

Referring to FIG. 11C, a third embodiment of a finger tensioner is illustrated having a finger cap 400B coupled to a plurality of longitudinal plates 436, 442 and 444. Each longitudinal plate is positioned adjacent a respective proximal, intermediate and distal phalange. Intermediate each longitudinal plate is a flexure 440 so that two adjacent flexures are positioned at each interphalangeal joint. One knuckle flexure 438 is positioned proximate the finger knuckle. Thus, as a finger is moved into flexion flexures 440 become compressed building restorative force between the adjacent flexures. In one preferred embodiment, the flexures are formed from spring steel. However, it should be understood that in other embodiments, the flexures and longitudinal plates may be formed from any suitable material.

Figure 11E:
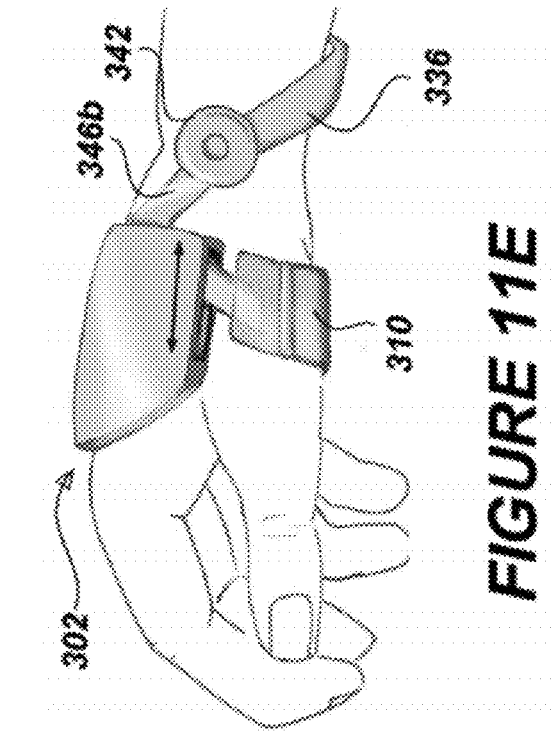
Figure 11D:
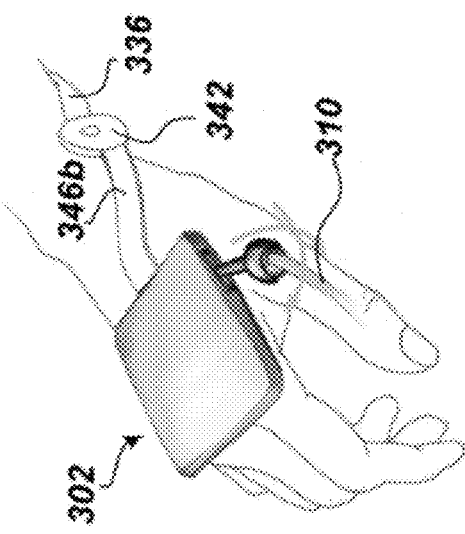

Referring to FIG. 11D, one preferred embodiment of a thumb tensioner 310 is shown coupled to hand support section 302 by a ball and socket joint. Referring to FIG. 11E, another preferred embodiment of a thumb tensioner 310 is shown coupled to hand support section 302 by a sliding pivoting joint that conforms to the inherent roll in the thumb about the distal proximal axis when the thumb goes into and out of flexion. The mechanism would provide a restorative force to the thumb moving it back into the extension position. In yet another preferred embodiment of a thumb tensioner (not shown) is coupled to the forearm support section by a ball and socket joint, sliding pivot joint, or any other connection point that mounts the thumb section to the forearm support.

In each finger tension mechanism discussed herein, suitable comfort pads (not shown) are positioned along the tension mechanism. In some embodiments, elastic finger sheaths conceal the finger assemblies on the ulna side of the finger assemblies. In other embodiments, the finger assemblies may be completely shielded depending on the use. It should also be understood that the sensors and electrodes described with respect to the embodiments shown in FIGS. 1-3 may also be used with the finger mechanism shown in FIGS. 11A-11C.

Referring again to FIG. 5, one of skill in the art should understand that forearm support section 304 is versatile and may be used with either a contracture type orthotic shown in FIGS. 6A-8 or with a mechanical finger assist type orthotic 304 shown in FIGS. 1-4 and 9A-11E. Thus, depending on the use of forearm support section 304, various types of padding and wrist hinges may be used.

Figure 12:
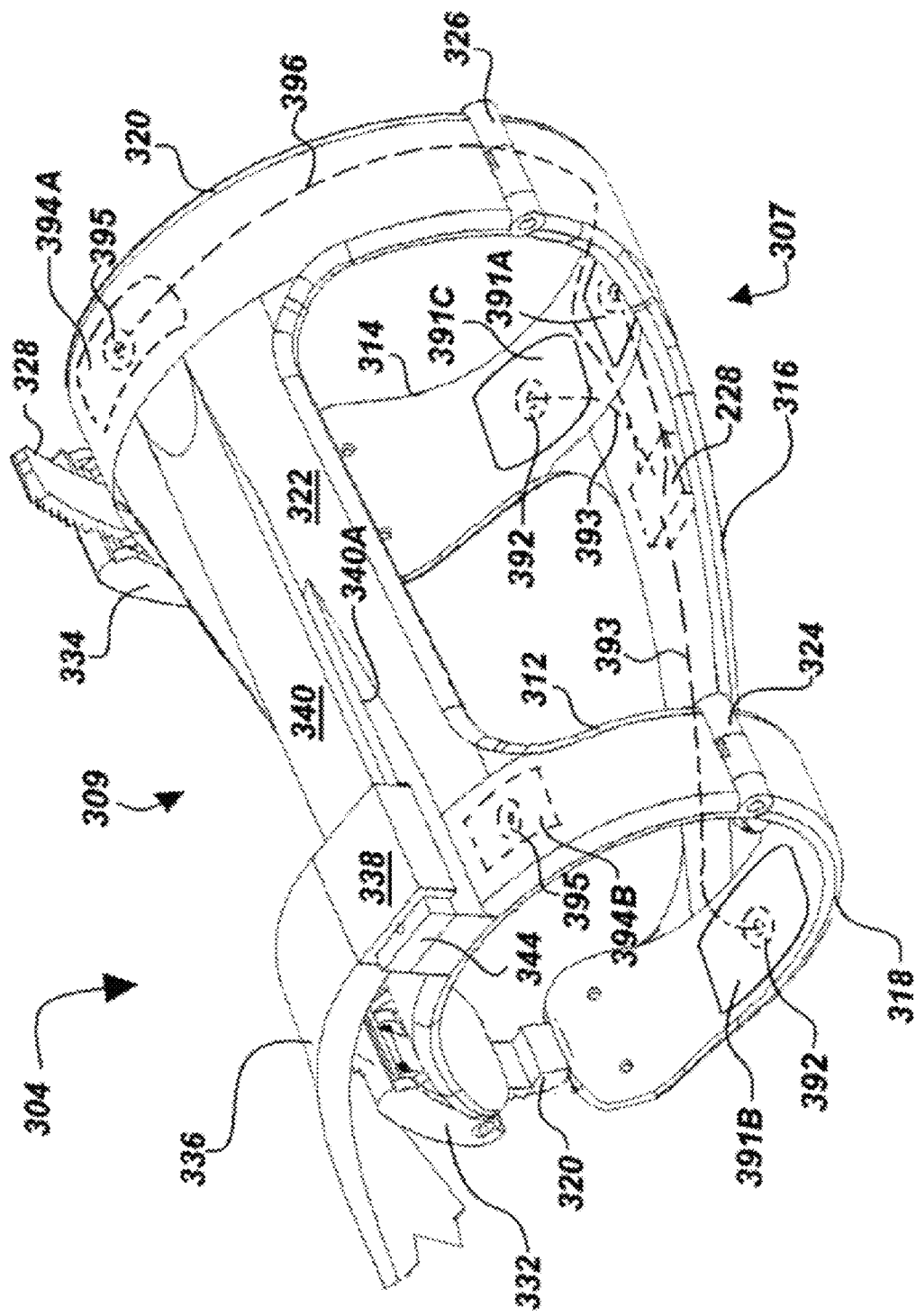
FIGS. 12-13 are perspective views of a forearm support section in accordance with one embodiment of the present invention for use with the neurological devices of FIGS. 4 and 6A-8.
Figure 13:
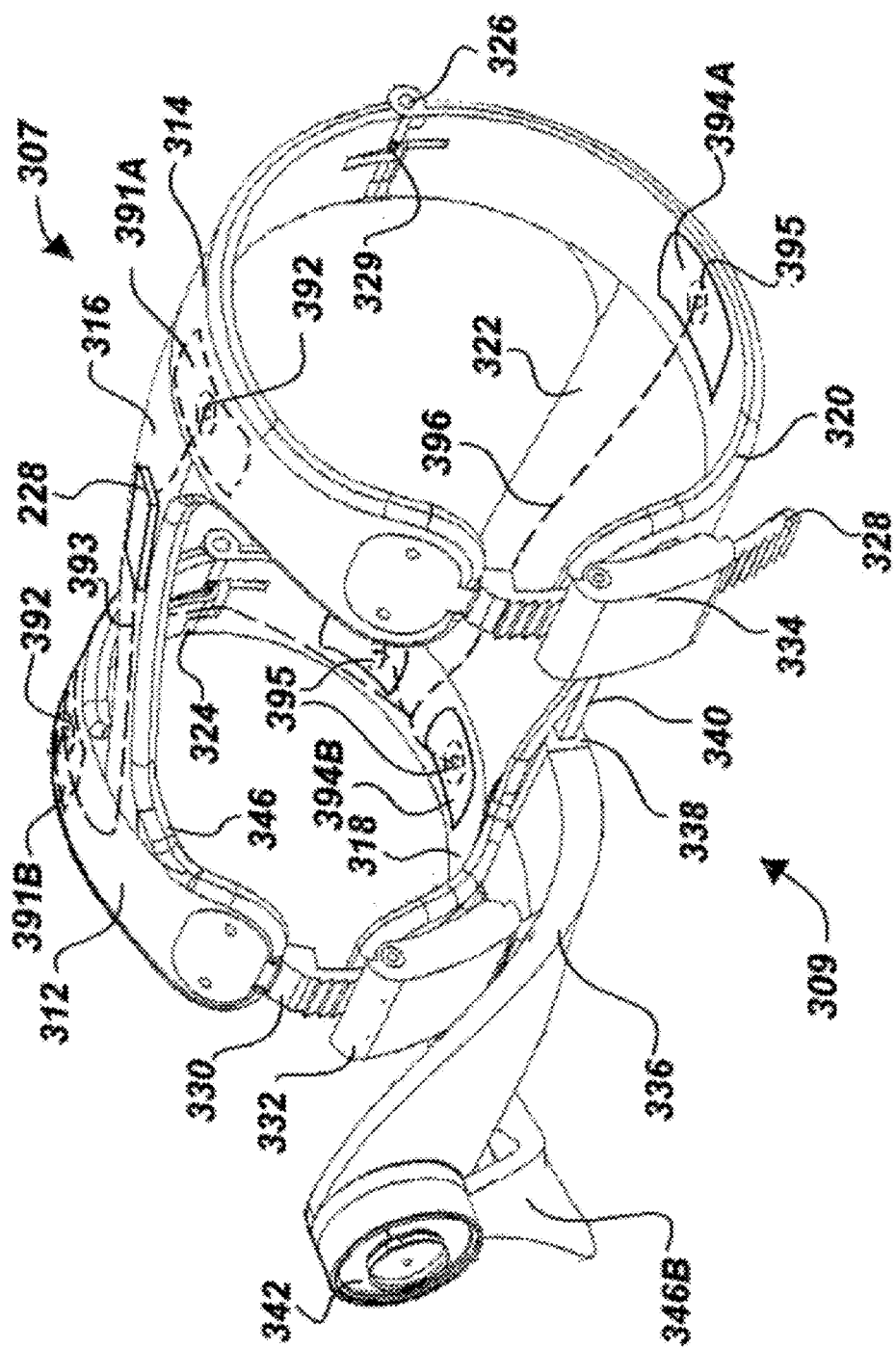

Referring to FIGS. 12 and 13, one preferred embodiment of forearm support section 304 is shown having electronic stimulation electrodes embedded in the forearm support section. In particular, electrodes 391 are positioned on an inner surface of forearm support section first half 307, and may also be positioned on an inner surface of forearm support section second half 309 (not shown) in some embodiments. More specifically, when forearm support section 304 is used in combination with the mechanical finger assist orthotic shown in FIGS. 1-4, electrodes 391A and 391B are embedded into forearm support section first half 307 and positioned so that a first electrode 391A stimulates the Extensor Digitorum Communis (EDC) and a second electrode 391B stimulates one of the Extensor Pollicis Brevis (EPB), the Extensor Pollicis Longus (EPL) or the Abductor Pollicis Longus (APL) depending on placement of the second electrode. Electrodes 391A and 391B are operatively coupled to data device 228 via wires 393 and through connectors 395. In one preferred embodiment, electrodes 391A and 391B are UltraStim Snap Electrodes Part No. US2020 manufactured by Axelgaard Manufacturing Co. Ltd., of Fallbrook, Calif. However, it should be understood by those skilled in the art that any suitable electrode may be used. Such electrodes may include, but are not limited to, a carbon impregnated silicon electrode, synthetic electrodes, gel based electrodes, water based electrodes, etc. In the embodiment shown in FIGS. 12 and 13, an optional electrode 391C is shown, which is also connected to data device 228 via connector 395 and wire 393 and may be positioned to provide electronic stimulation to any chosen muscle group depending on the operation of the orthotic.

In one embodiment of the present invention, data device 228 is configured to provide electrical stimulation to electrodes 391A, 391B and 391C, in addition to capturing rehabilitation data and monitoring muscle activity as described below. In other embodiments, a separate electrical stimulation controller may be used, which is either electrically isolated from data device 228 or operatively coupled to data device 228. In either case, in some preferred embodiments, the level of stimulation may be adjustable by either the user or the clinician by pushing a button (not shown) on either the electrical stimulation controller or the forearm shell. Also, the data device or electrical stimulation controller may be battery operated or it may plug into a wall outlet. If battery operated, the batteries may be rechargeable.

In addition to electrodes 391A, 391B and 391C, EMG sensors 394A and 394B are shown embedded into forearm support section second half 309 and positioned to monitor activity in one or more muscles which may include the Flexor Digitorum Superficilias (FDS) muscles in addition to the Flexor Pollicis Longus (FPL). An additional EMG sensor (not shown) may be embedded into hand piece 302 to monitor and sense activity in the Thenar muscle group of the hand. Thus, in one preferred embodiment, EMG sensors 394A and 394B monitor the flexor muscles, and when a predetermined threshold of muscle relaxation or deactivation is exceeded, data device 228 detects a trigger event and causes one or more of electrodes 391A, 391B and 391C to fire on the extensors muscles causing the extensor muscles to contract and to assist the mechanical finger tensioners in extending the fingers into an open hand position. Thus, EMG sensors 394A and 394B are used on antagonist muscles as an electronic trigger to cause electronic stimulation to be delivered to the agonist muscle group.

In another preferred embodiment, EMG sensors can be used on the agonist muscles as an electronic trigger to cause electrical stimulation in those same agonist muscles. The EMG sensors can be embedded on the forearm support section first half 307 and positioned to monitor activity of one or more muscles which may include Extensor Digitorum Communis, Extensor Pollicis Brevis (EPB), the Extensor Pollicis Longus (EPL) or the Abductor Pollicis Longus (APL). Thus, when a predetermined threshold of muscle contraction is exceeded, data device 228 detects a trigger event and causes one or more of the electrodes to fire the same muscles that were monitored.

In all of the embodiments involving electrical stimulation and/or EMG sensing, one of skill in the art should understand that the position of the electrodes and/or sensors may be positioned in various locations on the forearm support section depending on the particular rehabilitation needed. That is, the EMG sensors and electrical electrodes may all be positioned on forearm support section first half 307 or they may all be positioned on forearm support section second half 309. The actual position of one or more sensors and electrodes are determined by the clinician.

In some preferred embodiments, EMG sensors 394A and 394B may not be used. Instead, in these embodiments, electrical stimulation is fired during the release phase in a timed manner, for example 4 seconds on and 4 seconds off. The trigger event for the electronic stimulation may be manual in that the user or clinician may monitor the user's progress and provide a manual trigger for the electronic stimulation delivery. In other preferred embodiments, electronic stimulation may be triggered by sensors 222 and 224 (FIGS. 1 and 2) positioned along finger tension mechanism 308 or wrist hinge 342 (FIG. 13). When using sensors 222 and 224 as the triggering mechanism, data device 228 is programmed to detect an angular position of each joint in the fingers or wrist, and when a predetermined angular position is exceeded, for example greater than 45 degrees, data device 228 uses the sensor information as a trigger event to fire electrical stimulation at one or more of electrodes 391A, 391B and 391C. In other embodiments, other types of position sensors may be used in place of sensors 222 and 224. For example, spring gauges, bending sensors, strain gauges, pressure sensors, etc. may also be used in place of, or in addition to sensors 222 and 224.

Still referring to FIGS. 12 and 13, forearm support 304 with electronic stimulation and sensors may be used in combination with the contracture orthotic of FIGS. 6A-8. That is, the purpose of the orthotic of this embodiment is to stretch the contracted wrist and finger agonist muscles. Thus, for example, electrodes 391A, 391B and 391C may be positioned over the contracted agonist muscle groups (i.e., the flexor muscles so that the electrodes are embedded in forearm support section second half 309 in place of EMG sensors 394A and 394B) so that electronic stimulation may be delivered to the contracted muscles causing them to fatigue and relax. Relaxing the spastic muscles in combination with the stretching provided by contracture orthotic 304 allows the user to receive a greater stretch of the muscles to help increase range of motion.

In yet another preferred embodiment of the contracture orthotic of FIGS. 6A-8 in combination with the forearm support section of FIGS. 12 and 13, electrodes 391A, 391B and 391C can be positioned over agonist or antagonist muscle groups so that the delivery of electronic stimulation allows the user to strengthen their muscles while stretching. That is, electrodes 391A, 391B and 391C would be positioned in both of forearm support section first and second halves 307 and 309. The program can be set up so it alternates stimulation between the electrodes of first half 307 and the electrodes of second half 309. It can also target just the agonist or just the antagonist muscle groups. In some embodiments, the trigger event can be timed or caused by a manual trigger. It should be understood that the positioning of electrodes 391A, 391B and 391C may be anywhere on forearm support 304 depending on the application.

The combination of electrotherapy and a contracture orthotic device has many advantages over separate use of these technologies. Electrotherapy can reduce muscle inhibition to allow the orthotic to provide superior muscle stretch, and to eliminate the pain and discomfort sometimes experienced by wearing an orthotic. Muscle strengthening and re-education, muscle contraction inhibition, increased blood flow, nerve stimulation and neuro-pathway reconstruction, and other benefits can also be provided while the patient wears orthotic device 304 (FIG. 12) in combination with one or more of the hand plates of FIG. 8. The combination of electrical stimulation and orthotic therapy reduces the treatment time required during therapy. Moreover, many advantages stem from the combination of the two therapies. For example, the combination therapy inhibits contraction of the contracted muscles, tendons, and connective tissue to allow the orthotic device to provide "long effects" or permanent stretch therapy for a greater period relative to using only contracture therapy or electrical stimulation alone. Additionally, the combination therapy strengthens and re-educates the "antagonist" muscles to provide longer lasting permanent stretch and joint range of motion. By strengthening the antagonist muscle group opposing the shortened or contracted muscle group, the effect of the contracted muscles is diminished and the muscles are maintained in a stretched permanent position. In addition, by stimulating the muscles while on stretch, atrophy or muscle wasting is diminished. Combination therapy also enhances the development of new neuro-pathways to the brain so that muscle groups that are non-responsive to brain function can be significantly improved. Finally and most importantly, the combination of electrotherapy with orthotic stretch requires significantly less therapy or caregiver intervention to enhance therapy.

Figure 14A:
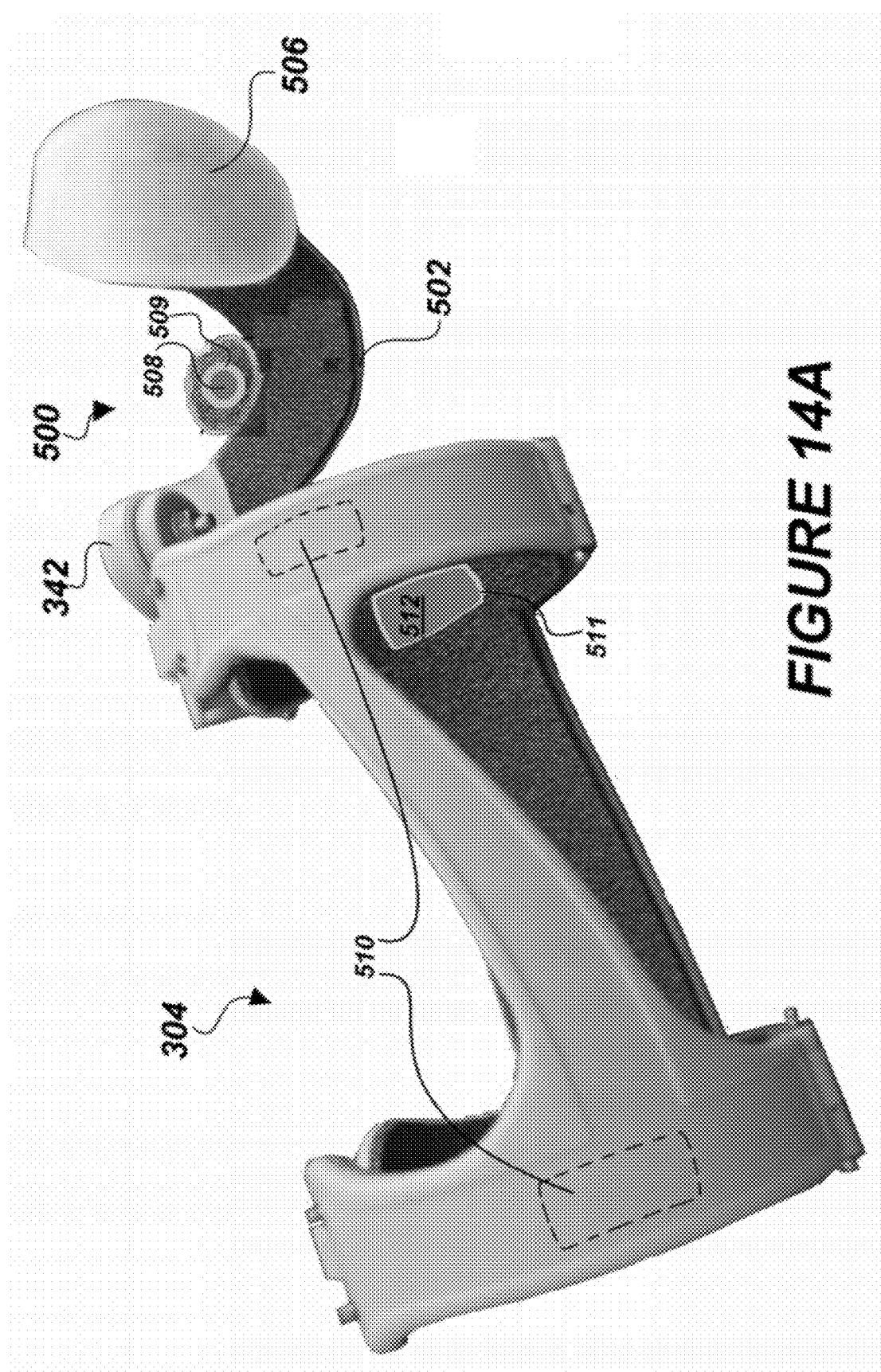
FIGS. 14A-14C are perspective views of a neurological device in accordance with another embodiment of the present invention.
Figure 14B:
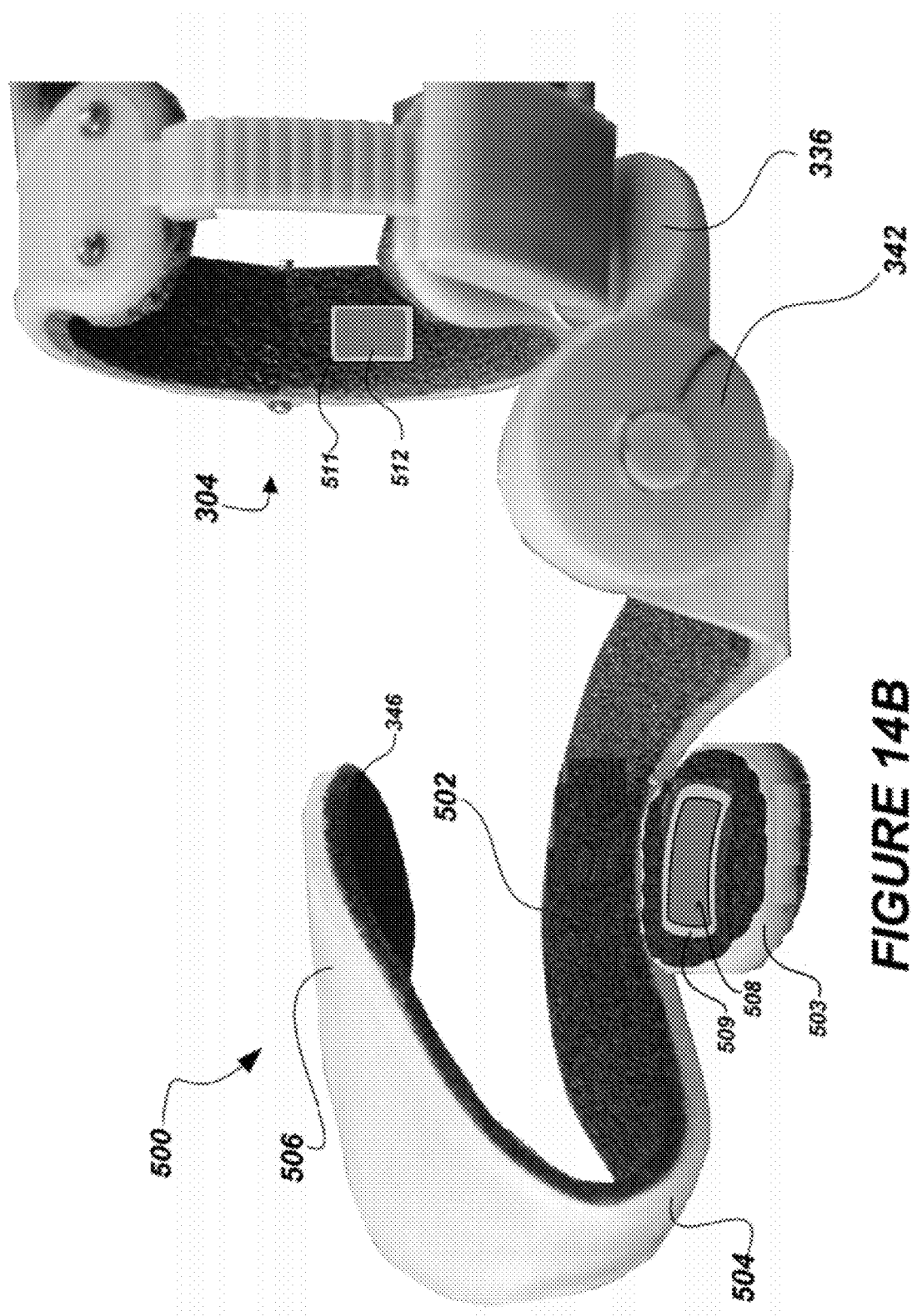
Figure 14C:
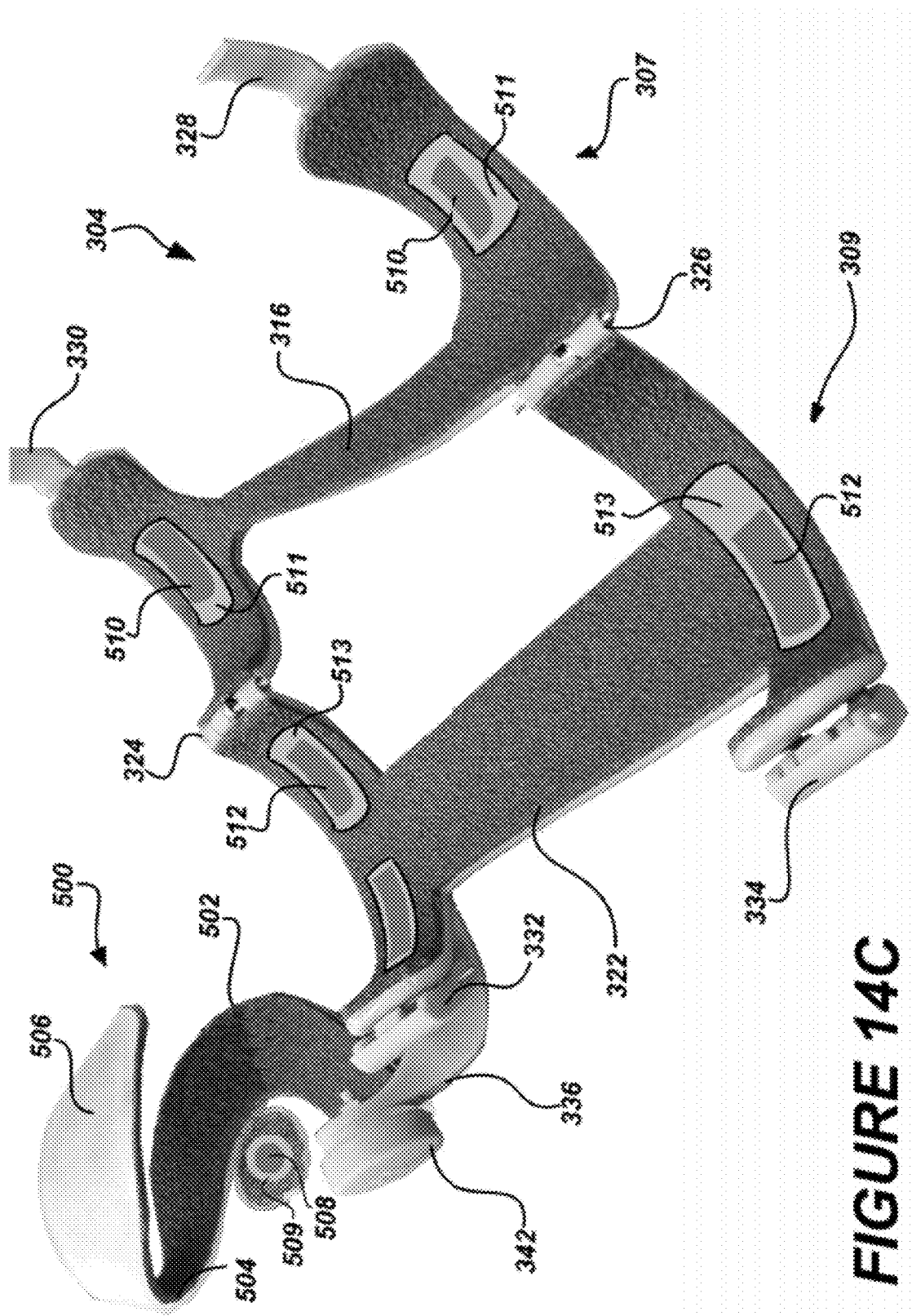

Referring to FIGS. 14A-14C, another orthotic is shown having a forearm support section similar to that of FIGS. 12 and 13 and a hand support section 500. For purposes of explanation, only the differences in the forearm support section will be referenced for brevity. Referring in particular to FIGS. 14A and 14B, hand support section 500 has a palmar portion 502 operatively coupled to wrist hinge 342 and a second end 506 that is positioned adjacent to the dorsum side of the user's hand. A curved intermediate portion 504 connects palmar portion 502 to the second end 506. The overall shape of hand support section 500 is C-shaped to cup the user's hand so that curved intermediate portion 504 extends between the user's thumb and forefinger. That is, when forearm support section 304 is donned on the user's arm, hand support section palmar portion 502 extends from the user's wrist across the palm side of the hand adjacent the thenar muscle group while hand support section second end 506 extends across the user's metacarpel bones between the knuckles and the wrist. In some embodiments, and additional adjustable metacarpel phalangeal (MCP) joint extension (not shown) is included that allows the user to extend the MCP joint extension over the users MCP joint to prevent hyperextension of the MCP joint during use of the orthotic.

Hand support section 500 may be formed from injected molded plastic that is flexible in nature. In other preferred embodiments, hand support section 500 may also be formed from other materials that are malleable. Padding 346 (FIG. 14B) may be attached on all underside surfaces of the molded plastic to ensure comfort when being worn. Moreover, a hand strap may be used to allow for snug fit. In other preferred embodiments of hand support section 500, other types of closure mechanisms may be used such as a ratchet or clam shell design. In some of these embodiments, the hand support section would be designed so that the user may slide their hand into the device and then apply pressure to the dorsum side of the hand support section to provide a snug fit. This type of design provides for ease in donning the device.

Multiple electrodes are embedded in hand support section 500 and forearm support section 304. In particular, various cutouts 509, 511 and 513 are formed in padding 346 during manufacturing of the orthotic device. Mounted in each cutout is a wired connector 392 (FIGS. 12 and 13) that is adapted to receive an electrode. Wires 393 (FIGS. 12 and 13) run between the injection molded plastic shell and padding 346 to conceal the wires and are coupled to data device 228 so that electrical stimulation may be delivered through the electrode. The use of the cutout and snap connector allow for variations in the placement of the electrodes based on the user's anatomy. In one preferred embodiment, snap connectors 392 are black snap adapters part no. SA1004 manufactured by Axelgaard Manufacturing Co. Ltd., of Fallbrook, Calif. It should be understood that the cutout and snap connectors of the present embodiment may also be used in combination with the forearm support section and electrodes and sensors described above with reference to FIGS. 12 and 13, and in any combination of the embodiments described herein.

Referring to FIG. 14C, in one preferred embodiment, electrodes 510 are mounted in cutouts 511 in forearm support section first half 307. Electrodes 512 are mounted in cutouts 513 in forearm support section second half 309. In this embodiment, two electrodes 510 are embedded in forearm support section first half 307 and two electrodes 512 are embedded in forearm support section second half 309. Furthermore, a hand support electrode 508 is mounted in a cutout 509 in an electrode mount coupled adjacent to hand support palmar portion 502, which may be either integrally formed with hand support palmar portion 502 or releasably coupled thereto. The hand support electrode stimulates the Thenar muscle group which is primarily responsible for thumb movement. In one preferred embodiment, the electrode mount is flexibly coupled to hand support palmar portion 502 to allow for movement of the Thenar muscle group. In another preferred embodiment, the electrode is attached to a flexible webbing or mesh-like material (not shown) which is connected to hand support palmar portion 502. In yet another embodiment, a thumb sleeve system (not shown) that houses the Thenar muscle electrode connects to the hand support palmar portion 502. It should be understood that any type of material can be used to house the electrode and connect to the hand support palmar portion 502. The location of each electrode is determined based on the muscle group to be stimulated. In one preferred embodiment, electrodes 508, 510 and 512 are Ultrastim Electrodes Part No. US2020, manufactured by Axelgaard Manufacturing Co. Ltd., of Fallbrook, Calif.

Each electrode is operatively coupled to data device 228, which in addition to being configured to capturing data, may also be configured to provide electrical stimulation over electrodes 508, 510 and 512. The data device may be configured to be manually triggered to provide electrical stimulation, contain programming that has timed triggers (i.e., on/off, alternating muscle group stimulation, etc.). Moreover, data device 228 may be customized to change the rate of the program, the pulse width, etc. In the alternative, separate from data device 228, an electrical stimulation controller may be mounted on forearm support 304 or mounted apart from the orthotic and operatively coupled to data device 228 or directly to the electrodes depending on the orthotic design. In either case, the data device or e-stimulation controller may be battery operated. If a manual trigger is used, the manual trigger may be wired or wireless. If an independent e-stimulation controller is used, the controller may be wired or wireless as well. In any of the preferred embodiments described herein, as an alternative to mounting the e-stimulation controller to the forearm or hand support sections, the controller may be releasably mounted to the patient using a bicep cuff. In this particular embodiment, the e-stimulation controller may be wired or wirelessly coupled to the orthotic. The bicep cuff may be formed from any suitable material such as spandex, pliable plastics with or without straps, elastomers or any combination thereof. The bicep cuff may be prefabricated or custom fabricated to particularly fit the user's bicep. In other embodiments, the e-stimulation controller may be attached to the user's body or clothing so as to limit entanglement with cords connected between the controller and the orthotic.

In other preferred embodiments, forearm support section 304 may also include EMG sensors as discussed with reference to FIGS. 12 and 13. That is, muscle activity in antagonistic muscles may be monitored and when activity level reaches a predetermined level, electrical stimulation is triggered at the agonist muscles. Or, in the alternative, the EMG sensors may be paired with a respective electrode to sense muscle activity in a muscle group, which when detected, causes the paired electrode to fire electrical stimulation in the same muscle group. That is, when muscle activity is sensed in the extensors and such activity reaches a predetermined level, electrical stimulation is delivered to the extensor muscles.

Although the forearm support section 304 of the present embodiment is shown having ratchet straps and ratchet covers, it should be understood that straps or other closing devices may be used in place of or in combination with the ratchets. Moreover, the forearm support section material and hand support section material may be malleable to assist in providing a custom fit for the user.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole and in part. For example, the forearm support section of FIGS. 12 and 13 may be used with the mechanical finger assist orthotic shown in FIGS. 1-4, 9A-9B and 10, with the contracture orthotic shown in FIGS. 6A-8 or without mechanical finger assist orthotic of FIGS. 14A-14B. Moreover, the biofeedback sensors disclosed in FIG. 3 may be combined with any other embodiment disclosed herein. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What we claim is:

1. An orthotic device comprising:
   a. a forearm support section that is configured to be releasably attached to a user's arm;
   b. a hand support section that is configured to be releasably attached to the user's hand;
   c. an adjustable joint coupled to the forearm support section and the hand support section, wherein the joint allows the hand support section to move in a sagittal plane with respect to the forearm support section;

d. at least one electromyography sensor coupled to the forearm support section and positioned to sense activity of one of an agonist muscle and an antagonist muscle in the user's arm;

e. at least one electrode coupled to the forearm support section and configured to provide electrical stimulation to the other of the agonist muscle and the antagonist muscle in the user's arm; and f. a controller operatively coupled to the at least one electromyography sensor and the at least one electrode, the controller being configured to deliver electrical stimulation to the at least one electrode, wherein the at least one electromyography sensor is configured to generate signals relating to activation or deactivation of the one of the agonist muscle and the antagonist muscle adjacent the at least one electromyography sensor, and the controller is configured to receive the signals relating to activation or deactivation of the one of the agonist muscle and the antagonist muscle, compare the signal to a predetermined threshold value and trigger delivery of electrical stimulation to the other of the agonist muscle and the antagonist muscle that is adjacent the at least one electrode based on the comparison.

2. The orthotic device of claim 1, further comprising at least one tensioner having a first end configured to be releasably coupled to a digit of the user's hand and an opposite second end coupled to the hand support section, wherein the tensioner is configured to be coupled to the user's digit at a first location and a second location, wherein the first and second locations are positioned longitudinally along the user's digit on opposite sides of the joint.

3. The orthotic device of claim 2, further comprising at least one sensor operatively coupled to one of the hand support section, the forearm support section and the tensioner, wherein the at least one sensor is configured to generate signals relating to a position of the user's arm.

4. The orthotic device of claim 2, further comprising at least one haptic feedback sensor operatively coupled to the at least one tensioner and configured to provide tactile sensation to the user's digit.

5. The orthotic device of claim 2, further comprising a plurality of sensors operatively coupled to the tensioner for determining a position of the user's digit, wherein when the position of the user's digit exceeds or falls below a predetermined position, electrical stimulation is triggered and delivered by the at least one electrode.

6. The orthotic device of claim 2, the hand support section further comprising an adjustment member for changing the tension provided by the tensioner.

7. The orthotic device of claim 1, wherein the at least one electromyography sensor is configured to be operatively coupled to the antagonist muscle and the at least one electrode is configured to be operatively coupled to the agonist muscle.

8. The orthotic device of claim 1, further comprising at least one haptic feedback sensor operatively coupled to one of the hand support section, the forearm support section and the adjustable joint, the haptic feedback sensor configured to provide tactile sensation.

9. The orthotic device of claim 1, further comprising a plurality of electrodes releasably mounted in the forearm support section and positioned to stimulate one of an agonist muscle group and an antagonist muscle group.

10. The orthotic device of claim 9, further comprising a plurality of electromyography sensors releasably mounted in the forearm support section and positioned to sense muscle activity in the other of the agonist muscle group and the antagonist muscle group that is related to the agonist muscle group.

11. An orthotic device comprising:

a. a forearm support section that is configured to be releasably attached to a user's arm;

b. a hand support section that is configured to be releasably attached to the user's hand;

c. at least one electromyography sensor coupled to the forearm support section and positioned to sense activity of one of an agonist muscle and an antagonist muscle in the user's arm;

d. at least one electrode coupled to the forearm support section and configured to provide electrical stimulation to the other of the agonist muscle and the antagonist muscle in the user's arm; and e. a controller operatively coupled to the at least one electrode, the controller being configured to deliver electrical stimulation to the at least one electrode, wherein the at least one electromyography sensor senses activity in the one of the agonist muscle and the antagonist muscle and the at least one electrode delivers electrical stimulation to the other of the agonist muscle and the antagonist muscle.

12. The orthotic device of claim 11, further comprising at least one tensioner having a first end configured to be releasably coupled to a digit of the user's hand and an opposite second end coupled to the hand support section, wherein the tensioner is configured to be coupled to the user's digit at a first location and a second location, wherein the first and second locations are positioned longitudinally along the user's digit on opposite sides of the joint.

13. The orthotic device of claim 12, further comprising at least one sensor operatively coupled to one of the hand support section, the forearm support section and the tensioner, wherein the at least one sensor is configured to generate signals relating to a position of the user's body.

14. The orthotic device of claim 12, further comprising a plurality of sensors operatively coupled to the tensioner for determining a position of the user's digit, wherein when the position of the user's digit exceeds or falls below a predetermined position, electrical stimulation is triggered and delivered by the at least one electrode.

15. The orthotic device of claim 12, the hand support section further comprising an adjustment member for changing the tension provided by the tensioner.

16. The orthotic device of claim 11, wherein the at least one electromyography sensor is coupled to the controller, the controller being configured to receive the signals relating to activation or deactivation of the one of the agonist muscle and the antagonist muscle, compare the signal to a predetermined threshold value and trigger delivery of electrical stimulation to the at least one electrode based on the comparison.

17. An orthotic device comprising:

a. a forearm support section;

b. a hand support section;

c. at least one electromyography sensor coupled to the forearm support section and adapted to be positioned adjacent one of an agonist muscle and an antagonist muscle of a user to sense activity in the one of the agonist muscle and the antagonist muscle of the user;

d. at least one electrode coupled to the forearm support section and adapted to be positioned to provide electrical stimulation to the other of the agonist muscle and the antagonist muscle of the user;

e. a controller operatively coupled to the at least one electrode, the controller being configured to deliver electrical stimulation to the at least one electrode; and f. at least one tensioner having a first end configured to be releasably coupled to a digit of the user's hand and an opposite second end configured to be coupled to the hand support section, wherein the tensioner is configured to be coupled to the user's digit at a first location and a second location, wherein the first and second locations are positioned longitudinally along the user's digit on opposite sides of the joint, wherein the at least one electromyography sensor senses activity in the one of the agonist muscle and the antagonist muscle and the at least one electrode delivers electrical stimulation to the other of the agonist muscle and the antagonist muscle.

18. The orthotic device of claim 17, further comprising at least one sensor operatively coupled to one of the hand support section, the forearm support section and the tensioner, wherein the at least one sensor is configured to generate signals relating to a position of the user's body.

19. The orthotic device of claim 17, further comprising a plurality of sensors operatively coupled to the tensioner for determining a position of the user's digit, wherein when the position of the user's digit exceeds or falls below a predetermined position, electrical stimulation is triggered and delivered by the at least one electrode.

20. The orthotic device of claim 17, the hand support section further comprising an adjustment member for changing the tension provided by the tensioner.

21. The orthotic device of claim 17, wherein the at least one electromyography sensor is coupled to the controller, the controller being configured to receive the signals relating to activation or deactivation of the one of the agonist muscle and the antagonist muscle, compare the signal to a predetermined threshold value and trigger delivery of electrical stimulation to the at least one electrode based on the comparison.

* * * * *